(12) United States Patent
Macri et al.

(10) Patent No.: US 11,116,441 B2
(45) Date of Patent: Sep. 14, 2021

(54) APPARATUS, METHOD, AND SYSTEM FOR PRE-ACTION THERAPY

(71) Applicants: Vincent John Macri, Tallahassee, FL (US); Vincent James Macri, New York, NY (US); Paul Zilber, Plainview, NY (US)

(72) Inventors: Vincent John Macri, Tallahassee, FL (US); Vincent James Macri, New York, NY (US); Paul Zilber, Plainview, NY (US)

( * ) Notice: Subject to any disclaimer, the term of this patent is extended or adjusted under 35 U.S.C. 154(b) by 0 days.

(21) Appl. No.: 16/173,250

(22) Filed: Oct. 29, 2018

(65) Prior Publication Data
US 2019/0099104 A1    Apr. 4, 2019

Related U.S. Application Data

(63) Continuation of application No. 14/595,673, filed on Jan. 13, 2015, now Pat. No. 10,111,603.
(Continued)

(51) Int. Cl.
*A61B 5/375* (2021.01)
*A61B 5/00* (2006.01)
(Continued)

(52) U.S. Cl.
CPC ............ *A61B 5/375* (2021.01); *A61B 5/4041* (2013.01); *A61B 5/4519* (2013.01);
(Continued)

(58) Field of Classification Search
CPC ... A61B 5/0482; A61B 5/4041; A61B 5/4519; A61B 2505/09; G16H 20/30; G16H 50/50; G06F 19/3481
See application file for complete search history.

(56) References Cited

U.S. PATENT DOCUMENTS

| 5,078,152 A | 1/1992 | Bond et al. |
| 5,429,140 A | 7/1995 | Burdea et al. |

(Continued)

FOREIGN PATENT DOCUMENTS

| JP | 2002306632 A | 10/2002 |
| KR | 20120137327 A | 12/2012 |

(Continued)

OTHER PUBLICATIONS

Macri et al., "Repairing Brain-Motor Disability," International ABI Clinical Study Czech Republic Poster, (c)2015, 1 page.
(Continued)

*Primary Examiner* — Sundhara M Ganesan
(74) *Attorney, Agent, or Firm* — Resolute Legal, PLLC

(57) ABSTRACT

Embodiments of the present disclosure provide an apparatus, method and system for physical, pre-action, extremity and related spinal cord, brain stem and neural therapies. An apparatus according to the present disclosure can include: a computing device configured to convert an input control action into a simulation instruction, wherein the input control action is provided by an input device; at least one simulated extremity operatively connected to the computing device and configured to simulate at least one modeled human anatomical movement based on the simulation instruction, wherein the at least one modeled human anatomical movement is distinct from the input control action; and a feedback device operatively connected to the computing device and configured to transmit a sensory response, wherein the sensory response is based on the modeled human anatomical movement.

35 Claims, 5 Drawing Sheets

Related U.S. Application Data

(60) Provisional application No. 61/926,551, filed on Jan. 13, 2014.

(51) Int. Cl.
    *G16H 50/50*        (2018.01)
    *G16H 20/30*        (2018.01)
    *G16H 40/63*        (2018.01)

(52) U.S. Cl.
    CPC .......... *A61B 2505/09* (2013.01); *G16H 20/30* (2018.01); *G16H 40/63* (2018.01); *G16H 50/50* (2018.01)

(56) References Cited

U.S. PATENT DOCUMENTS

| | | |
|---|---|---|
| 5,554,033 A | 9/1996 | Bizzi et al. |
| 5,846,086 A | 12/1998 | Bizzi et al. |
| 5,984,880 A | 11/1999 | Lander et al. |
| 6,057,846 A | 5/2000 | Sever, Jr. |
| 6,098,458 A | 8/2000 | French et al. |
| 6,162,189 A | 12/2000 | Girone et al. |
| 6,164,973 A | 12/2000 | Macri et al. |
| 6,421,048 B1 | 7/2002 | Shih et al. |
| 6,666,831 B1 | 12/2003 | Edgerton et al. |
| 6,749,432 B2 | 6/2004 | French et al. |
| 6,827,579 B2 | 12/2004 | Burdea et al. |
| 7,179,234 B2 | 2/2007 | Nashner |
| 7,252,644 B2 | 8/2007 | Dewald et al. |
| 7,460,125 B2 | 12/2008 | Yang et al. |
| 7,731,500 B2 | 6/2010 | Feygin et al. |
| 7,993,291 B2 | 8/2011 | Karkanias et al. |
| 8,214,029 B2 | 7/2012 | Koeneman et al. |
| 8,496,564 B2 | 7/2013 | Zlobinsky |
| 8,834,169 B2 | 9/2014 | Reinkensmeyer et al. |
| 9,271,660 B2 | 3/2016 | Luo et al. |
| 9,326,909 B2 | 5/2016 | Liu et al. |
| 9,403,056 B2 | 8/2016 | Weinberg et al. |
| 10,380,910 B2 | 8/2019 | Wu et al. |
| 2002/0120362 A1 | 8/2002 | Lathan et al. |
| 2002/0146672 A1 | 10/2002 | Burdea et al. |
| 2004/0254771 A1 | 12/2004 | Riener et al. |
| 2004/0267320 A1 | 12/2004 | Taylor et al. |
| 2005/0250083 A1 | 11/2005 | Macri et al. |
| 2006/0074822 A1 | 4/2006 | Eda et al. |
| 2006/0084050 A1 | 4/2006 | Haluck |
| 2006/0287617 A1 | 12/2006 | Taub et al. |
| 2007/0016265 A1 | 1/2007 | Davoodi et al. |
| 2007/0048702 A1 | 3/2007 | Jang et al. |
| 2007/0066918 A1 | 3/2007 | Dewald et al. |
| 2007/0126733 A1 | 6/2007 | Yang et al. |
| 2008/0009771 A1 | 1/2008 | Perry et al. |
| 2008/0132383 A1 | 6/2008 | Einav et al. |
| 2009/0221928 A1 | 9/2009 | Einav et al. |
| 2009/0259148 A1 | 10/2009 | Willmann et al. |
| 2009/0326341 A1 | 12/2009 | Furlan |
| 2011/0009241 A1 | 1/2011 | Lane et al. |
| 2011/0054870 A1 | 3/2011 | Dariush et al. |
| 2012/0004579 A1 | 1/2012 | Luo et al. |
| 2012/0021394 A1 | 1/2012 | deCharms |
| 2012/0077163 A1 | 3/2012 | Sucar Succar et al. |
| 2012/0108909 A1 | 5/2012 | Slobounov et al. |
| 2012/0142416 A1 | 6/2012 | Joultras |
| 2012/0157263 A1 | 6/2012 | Sivak et al. |
| 2013/0035734 A1 | 2/2013 | Soler Fernandez et al. |
| 2013/0046206 A1 | 2/2013 | Preminger |
| 2013/0072353 A1 | 3/2013 | Alessandri et al. |
| 2013/0096940 A1 | 4/2013 | Hayes |
| 2013/0123667 A1 | 5/2013 | Komatireddy et al. |
| 2013/0138011 A1 | 5/2013 | Ang et al. |
| 2013/0171596 A1 | 7/2013 | French |
| 2013/0252216 A1 | 9/2013 | Clavin et al. |
| 2013/0316316 A1 | 11/2013 | Flavell et al. |
| 2014/0004493 A1 | 1/2014 | Macri et al. |
| 2014/0031098 A1 | 1/2014 | Tacconi |
| 2014/0287876 A1 | 9/2014 | Etter et al. |
| 2014/0364230 A1 | 12/2014 | Borghese et al. |
| 2014/0371633 A1 | 12/2014 | Evin et al. |
| 2015/0196800 A1 | 7/2015 | Macri et al. |
| 2015/0202492 A1 | 7/2015 | Domansky et al. |
| 2016/0082319 A1 | 3/2016 | Macri et al. |
| 2016/0086500 A1 | 3/2016 | Kaleal, III |
| 2016/0129343 A1 | 5/2016 | Domansky et al. |
| 2016/0213978 A1 | 7/2016 | Ban et al. |
| 2016/0235323 A1 | 8/2016 | Tadi et al. |
| 2017/0209737 A1 | 7/2017 | Tadi et al. |
| 2017/0325719 A1 | 11/2017 | Courtine et al. |
| 2018/0184948 A1 | 7/2018 | Tadi et al. |
| 2018/0228430 A1 | 8/2018 | Perez Marcos et al. |
| 2018/0229081 A1 | 8/2018 | Yi et al. |
| 2018/0239430 A1 | 8/2018 | Tadi et al. |
| 2018/0239956 A1 | 8/2018 | Tadi et al. |
| 2018/0240261 A1 | 8/2018 | Tadi et al. |
| 2018/0262744 A1 | 9/2018 | Tadi et al. |
| 2018/0275760 A1 | 9/2018 | Nicolet et al. |
| 2018/0275766 A1 | 9/2018 | Condolo |
| 2018/0336973 A1 | 11/2018 | Tadi et al. |
| 2019/0009133 A1 | 1/2019 | Mettler May |
| 2019/0025919 A1 | 1/2019 | Tadi et al. |

FOREIGN PATENT DOCUMENTS

| | | |
|---|---|---|
| WO | 2011123059 A1 | 10/2011 |
| WO | 2012161657 A1 | 11/2012 |
| WO | 2013136287 A1 | 9/2013 |
| WO | 2014/154839 A1 | 10/2014 |
| WO | 2016/081830 A1 | 5/2016 |
| WO | 2018/134686 A3 | 7/2018 |
| WO | 2018/142228 A2 | 8/2018 |
| WO | 2018/146546 A1 | 8/2018 |
| WO | 2018/146558 A3 | 8/2018 |

OTHER PUBLICATIONS

International Search Report dated Oct. 14, 2014, International Application No. PCT/US2014/038447, pp. 1-4.

Lebedev M.A., et al., "Brain-Machine Interfaces: Past, Present and Future" Trends in Neurosciences vol. 29, No. 9, Sep. 2006, pp. 536-546.

Extended European Search Report dated Jul. 9, 2020, European Patent Application No. 19207843.4, pp. 1-9.

Ultraleap, Leap Motion Developer, Retrieved from the Internet on Aug. 5, 2020: https://developer.leapmotion.com/documentation, pp. 1-14.

Biospace, "Robotic Stroke Therapy Devices from Kinetic Muscles Inc. to be Marketed Internationally", Mar. 23, 2010, Retrieved from the Internet: https://www.biospace.com/article/releases/robotic-stroke-therapy-devices-from-b-kinetic-muscles-inc-b-to-be-marketed-internationally-/, pp. 1-3.

Jeffrey Rogers et al., "Elements virtual rehabilitation improves motor, cognitive, and functional outcomes in adult stroke: evidence from a randomized controlled pilot study" ,Journal of NeroEngineering and Rehabilitation, vol. 16, No. 56, 2019, pp. 1-13.

Neofect, Retrieved from the Internet Apr. 2020: https://www.neofect.com/en/product/stroke-therapy-hand/, pp. 1-9.

Ayca Utkan Karasu et al., "Effectiveness of Wii-based rehabilitation in stroke: A randomized controlled study", Journal of Rehabilitation Medicine, vol. 50, No. 5, May 2018, pp. 406-412.

Jintronix, Retrieved from the Internet Apr. 2020: http://www.jintronix.com/, pp. 1-18.

Virtualis, "Functional Rehabilitation", Retrieved from the Internet Apr. 2020: https://virtualisvr.com/en/functional-rehabilitation/, pp. 1-20.

XRhealth, Retrieved from the Internet Apr. 2020: https://www.xr.health/, pp. 1-13.

Constant Therapy, Retrieved from the Internet Apr. 2020: https://thelearningcorp.com/constant-therapy/, pp. 1-7.

Bioness, Retrieved from the Internet Apr. 2020: https://www.bioness.com/BITS.php, pp. 1-3.

(56) References Cited

OTHER PUBLICATIONS

TRC, Retrieved from the Internet Apr. 2020: https://www.trcare.net/product, pp. 1-3.
Bertec, "Prime IVR", Retrieved from the Internet Apr. 2020: https://www.bertec.com/products/prime-ivr, pp. 1-9.
Rehab-Robotics, Retrieved from the Internet Apr. 2020: http://www.rehab-robotics.com.hk/hoh/index.html, p. 1.
Myomo, Retrieved from the Internet Apr. 2020: https://myomo.com/what-is-a-myopro-orthosis/, p. 1-6.
Kinetec, "Continuous Passive Motion", Retrieved from the Internet Apr. 2020: https://kinetecuk.com/categories/continuous-passive-motion, p. 1-4.
Chattanooga Rehab, Retrieved from the Internet Apr. 2020: https://www.chattanoogarehab.com/us/, pp. 1-9.
Daiya, Power Assist Glove, Retrieved from the Internet Apr. 2020: https://www.daiyak.co.jp/en/product/detail/280?k=assist+glove&s=0, p. 1-6.
Neofect, "Neomano", Retrieved from the Internet Apr. 2020: https://www.neofect.com/us/neomano, pp. 1-13.
The Medcom Group, Ltd, "QAL Medical 6000X WaveFlex Hand CPM", Retrieved from the Internet Apr. 2020: https://www.medcomgroup.com/qal-medical-6000x-waveflex-hand-cpm/, pp. 1-7.

APPARATUS, METHOD, AND SYSTEM FOR PRE-ACTION THERAPY

RELATED APPLICATIONS

This application is a continuation of U.S. patent application Ser. No. 14/595,673, filed Jan. 13, 2015, which is hereby incorporated by reference and which claims priority to U.S. Provisional Patent Application No. 61/926,551 filed Jan. 13, 2014, which is hereby incorporated by reference.

BACKGROUND

The present invention relates to pre-action therapy for individuals who are disabled, impaired or handicapped from making therapeutic physical movements. Pre-action therapy users engage in virtual anatomical interactivity to improve motor performance of body parts without the user being required to perform actual, therapeutic physical movements. Particularly, the present invention is directed to pre-action therapy, synonymously virtual anatomical interactivity therapy and/or premotor therapy, for re-gaining motor control of body parts, e.g., upper and/or lower extremities due to acquired brain injury or other brain-motor control disablement. The present invention includes systems, methods, program products and apparatuses for rehabilitation of paresis or paralysis. Further, the present invention includes particular types of activities such as feedforward and feedback directed toward user input-controlled movements of virtual extremities, such as anatomically realistic virtual extremities with analogous true range of motion, which can simulate human physical movements. The present invention further relates to combinations of pre-action therapy coupled to therapeutic physical activities.

SUMMARY

A first aspect of the present disclosure provides an apparatus for physical, pre-action, extremity and related spinal cord, brain stem and neural therapies. The apparatus can include: a computing device configured to convert an input control action into a simulation instruction, wherein the input control action is provided by an input device; at least one simulated extremity operatively connected to the computing device and configured to simulate at least one modeled human anatomical movement based on the simulation instruction, wherein the at least one modeled human anatomical movement is distinct from the input control action; and a feedback device operatively connected to the computing device and configured to transmit a sensory response, wherein the sensory response is based on the modeled human anatomical movement.

A second aspect of the present disclosure provides a method for physical, pre-action, extremity and related spinal cord, brain stem and neural therapies, the method comprising: translating an input control action into a simulation instruction for at least one modeled human anatomical movement, wherein the at least one modeled human anatomical movement is distinct from the input control action; simulating, with at least one simulated extremity, the at least one modeled human anatomical movement based on the simulation instruction; calculating a difference between an ideal movement and the at least one modeled anatomical movement; and transmitting a sensory response to a user, wherein the sensory response is derived from the calculated difference.

A third aspect of the present disclosure provides a system for physical, pre-action, extremity and related spinal cord, brain stem and neural therapies. The system can include: an input device configured to receive an input control action from a user; at least one simulated extremity operatively connected to the input device and configured to simulate at least one modeled human anatomical movement based on the input control action; a feedback device operatively connected to the input device and configured to transmit a sensory response to the user; and a computing device operatively connected to the input device, the at least one simulated extremity and the feedback device, wherein the computing device is configured to perform actions including: simulate, with the at least one simulated extremity, the at least one modeled human anatomical movement based on the input control action, wherein the at least one modeled human anatomical movement is distinct from the input control action, calculate a difference between an ideal movement and the modeled human anatomical movement and transmit a sensory response via the feedback device to a user, wherein the sensory response is derived from the calculated difference.

BRIEF DESCRIPTION OF THE DRAWINGS

These and other features of this invention will be more readily understood from the following detailed description of the various aspects of the invention taken in conjunction with the accompanying drawings.

Figure 1:
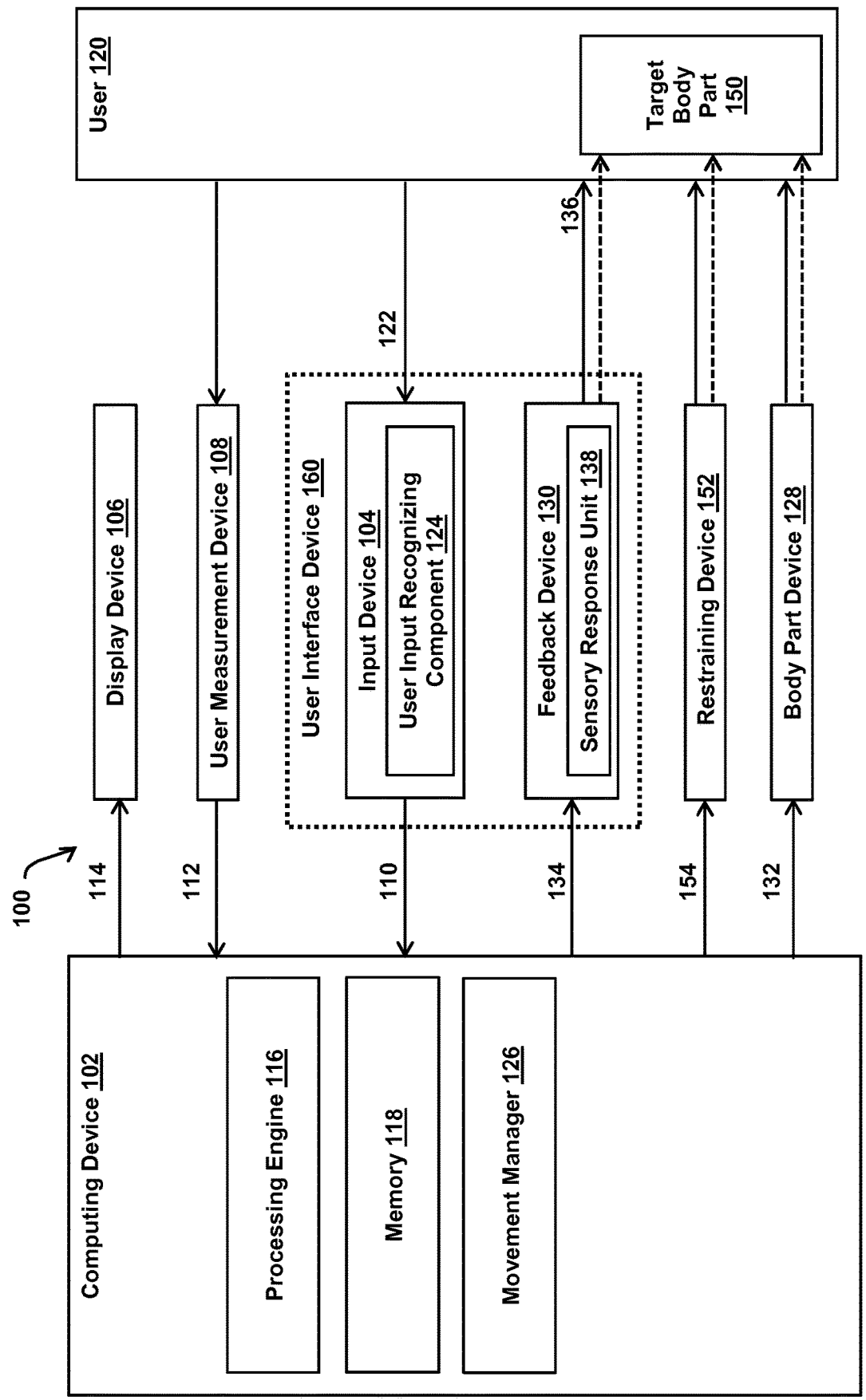
FIG. 1 depicts an illustrative system for pre-action therapy synonymously premotor, virtual anatomical interactivity and related physical therapy, according to an embodiment of the present disclosure.

The drawings are merely schematic representations, not intended to portray specific parameters of the invention. The drawings are intended to depict only typical embodiments of the invention and therefore should not be considered as limiting the scope of the invention. In the drawings, like reference numbering represents like elements.

DETAILED DESCRIPTION

Embodiments described herein relate to pre-action therapy ("P-AT") using methods and apparatuses that provide for users' control of virtual human body parts (e.g., extremities). Further embodiments relate to the present invention in conjunction with demonstrated therapeutic physical movements and exercises such as those used in physical and occupational therapies. Embodiments of the present disclosure include activation of at least one device attached or unattached to at least one human body part such that as the user controls the virtual body part(s), at least one such device is simultaneously activated to stimulate one or more of the user's physical body parts, therefore combining physical and occupational therapies with pre-action therapy. Additional embodiments pertain to the field of simulations for user pre-action therapy, i.e., systems which provide for input to pre-action therapy separate from or in conjunction with physical action exercise and/or methods that provide for user control of virtual body parts.

Embodiments of the present disclosure include P-AT and interactive P-AT activity ("iP-ATA") related to physical and occupational therapy. Physical and occupational therapies in assisted or unassisted modes include control and manipulation of individuals' body parts ("extremities") in order to regain, i.e., rehabilitate, purposeful physical motor functions. Physical and occupational therapies are directed, in part, to helping individuals solve their problem of regaining or improving control of disabled, impaired or handicapped extremities. The problem addressed by P-AT/iP-ATA is individuals regaining or improving control of disabled, impaired or handicapped extremities without and before the individuals can move the extremities. The problem is exacerbated by hemiplegia, paraplegia, quadriplegia, paresis, other paralysis or injury affecting motor function of the extremities. The problem addressed by P-AT/iP-ATA is mis-addressed and/or under-addressed by virtual reality ("VR") technologies that fail to provide disabled, impaired or handicapped individuals with control over virtual extremities. For example, motion capture by any of several technologies (optical, magnetic, acoustic, etc.) can include the full or partial movement of a human subject captured and recorded, typically by a computer system. The subject makes actual first person movements or actions. Resultant data points represent the actual body position of joints and/or limbs (or other components) in two-dimensional or three-dimensional space, either statically as a snapshot or dynamically over time. Motion capture is irrelevant to individuals who cannot move their extremities.

Further and marginally relevant are goal-driven computer animation systems containing a body model which receives target goals from a subject directing a first or third person pre-programmed action-to-goal. The goal driven system calculates, e.g., using inverse kinematics, necessary body positions and orientations for the animated body model to achieve. Goal driven systems conflict with P-AT/iP-ATA's user-driven idiomatic control of virtual extremities which are anatomically realistic with analogous true range of motion; i.e., the goal driven system provides the control, not the user. A goal driven system executes a virtual movement which completely bypasses the physical and occupational therapy paradigm of an individual making a therapeutic physical movement. Physical and occupational therapists advise, guide, or act to directly control patients' extremities. The present invention discloses direct user control of virtual extremities by receiving specific user inputs, i.e., pointing a cursor to virtual joints and dragging the associated extremity to a desired body position and orientation by non-corresponding (standard computer input, e.g., by mouse, keyboard, etc.) pre-action activities. In other words, the user controls virtual extremities and need not make (since she/he cannot move an extremity) a physical extremity movement in order for a simulated physical movement to occur. In P-AT/iP-ATA, virtual extremities can have model movements, but they are completely user controllable images of body parts programmed to simulate physical movements and actions according to each user's custom, idiomatic control and direction. As such, P-AT/iP-ATA is consistent with and relevant to physical and occupational therapies and individuals who are disabled, impaired or handicapped from making therapeutic physical movements.

Embodiments of the present invention enable individuals, e.g., a user or a plurality of users, to use self-controlled and/or synonymously self-directed pre-action therapy simulations to stimulate brain structures, cortices, synapses and processes. Operationally, a user can control virtual body parts that are anatomically realistic with analogous true ranges of motion to simulate physical movements and actions, thereby engaging in pre-action therapy simulations. Further, embodiments of the present disclosure include providing particular types of feedback to the user based on distinct input controlled movements which may or may not correspond to a user's proficiency and/or the displaying of virtual body part movements.

Before or without being able to perform physical action(s), a user can use input control using without limitation any input means, e.g., a computer (hand or foot) mouse, keyboard, controller, touch-screen, head or eye actions, voice control, hand waving actions, measurement of brain signals (e.g., electrical and/or measured neurological signals), etc., whether transmitted by wired or wireless signals) that control/direct simulated physical movements and actions of on-screen or holographic images or physical devices. A user's physical method of input can be physically distinct from virtual physical aspects, appearance and/or versions of the simulated actions of on-screen or holographic images or physical devices. As used herein, the term "simulate" and its related forms can refer to the display or demonstration of any action or group of actions in which a model (virtual or physical) or image provided on, e.g., a display device, performs a particular movement, motion, action, animation, etc. In addition, a "simulated extremity" can refer to a wholly virtual extremity, a physically simulated or modeled extremity such as a robotic extremity and/or combinations thereof. Simulated actions can be at least partially manipulated or performed by a user. The user's inputs can control any virtual body parts, whether clothed, skin-covered, exposed, or simulated in any real or virtual environment. User inputs can control/direct or otherwise manipulate virtual body parts contemporaneously or simultaneously and/or activate at least one device attached or unattached to at least one human body part, such that the device activates or stimulates one or more of the user's corresponding or non-corresponding actual (i.e., physical) body parts.

Physiologically, a user's disability, impairment or handicap challenge may be to initiate or improve physical or related neural actions before or without being able to perform or practice those actions. The present invention can be used for self or assisted therapy without limitation: to enable performing without limitation virtual and/or new actions or improving past actions; for improving the user's ability to execute various physical movements, actions, skills and techniques; for potentiation of processes for replacement or supplementation of damaged neural circuits (e.g., help joint-replacement patients regain abilities); for de-activation of existing neuromuscular actions (e.g., to decrease or stop users' uncontrolled muscle contractions); for de-sensitization of damaged neural circuits (e.g., actuating painful body parts); and/or for creation of synaptic processes to supplant dysfunctional and/or debilitating experiences (e.g., suffering from phobias, schizophrenic hallucinations, autism spectrum disorder or other sensory-action disorder).

Existing theories hold that repeated stimulation of neurological receptors may form "cell assemblies" and there are beneficial mathematical relationships between outcomes of repeated firing of interconnected neurological cells, synaptic formations and learned behavior physical movements. Embodiments of the present invention at least include and provide for repeated, self-induced neurological stimulation and self-therapy, including neurological improvements by combining particular types of feedback with particular types of user inputs.

Using an embodiment of the present invention, the user may control simulated physical movements and actions. Whether the user's attempt succeeds, partially succeeds or fails, embodiments of the present disclosure can provide virtual and/or physical action-specific feedback to the user based on her/his degree of success or failure, which may be defined as a "proficiency" or "movement proficiency" or "action proficiency." Consequently, the user's processes for anticipated intended and physical movements and/or actions and related processes are activated. This activation may be followed by controlling and/or directing simulated actions. Using embodiments of the present invention, in which the user receives physical sensation feedback, may help to illustrate and reinforce what the user actually did. Repetition, by using the present invention, in addition to feedback tracked to the user's evolution in performance, can improve the user's abilities and can reinforce the user's self-therapy by repeating positive physical sensation feedback and/or reducing and eliminating negative physical sensation feedback.

Epidemiologically and by way of example, the combined, annual incidence of ABI, stroke and TBI alone, in the United States affects about 2.5 million survivors annually. A broader category, neurotrauma (penetrating and non-penetrating), including primary brain tumor, focal dystonias, limb apraxia/ataxia, cerebral palsy and amputations, annually affects more than 12 million U.S. civilians and approximately 200,000-400,000 combat veterans. Assuming that the incidence of ABI/TBI alone is generally uniform worldwide, by extrapolation the total number of ABI/TBI survivors worldwide would therefore exceed 275 million individuals, which represents a number approximating the entire U.S. population. The total number of spinal cord injury survivors in the United States is approximately 200,000-250,000 and over 3,000,000 worldwide.

Purposeful and reflexive physical actions of body parts are proximally derived from neuronal signaling (spinal cord outputs) to muscles. However, pre-action therapy for purposeful actions is derived from neuronal signaling (outputs) of brain structures or processes initiating neuronal signaling to the spinal cord. Brain communications allow users to initiate purposeful new physical actions or to regain the ability to perform said physical actions or to correct physical, neurological or psychological actions associated with disorders or conditions.

The damaged brain, no less than other damaged body parts, requires therapy or rehabilitation. P-AT/iP-ATA stimulate brain-motor-control activity. No known virtual anatomical interactive technologies other than those disclosed in this disclosure are directed to pre-action therapy in virtual environments. An example implementation of the systems and methods described herein can apply to persons suffering from brain-motor-control and sensory-related diseases and/or injuries. Acquired brain injury ("ABI"), including stroke, chronic traumatic encephalopathy, spinal cord injury and traumatic brain injury ("TBI"), survivors or without limitation individuals affected by any disabling, damaged or dysfunctional condition, disorder, or experience may sustain impaired or eliminated use of one or more body parts. The result is formation of mild to severe barriers to physically controlling one's movements, actions and environment. The barriers exist despite, in many instances, body parts being completely or partially physically uninjured. For ABI survivors it is fair to say that except for the brain injury (and consequential extremity atrophy) chronic physical action deficits in the extremities would not require rehabilitation. To address said deficits, ABI survivors undergo long-term and costly therapeutic and rehabilitative procedures. These are major healthcare services and/or cost problems.

Conventional rehabilitation/therapies for treating ABIs are primarily physical movement in nature involving assisted and independent efforts to restore survivors to being able to make unaffected physical movements and actions. Physical and occupational therapy actions are characterized in that the movements of survivors' body parts correspond to unaffected, therefore rehabilitative movements. For example, when a survivor recovering from a stroke or TBI undergoes rehabilitation to regain proper axial movement of the survivor's arm at the shoulder, the survivor with or without assistance repeatedly attempts to move (or have moved with professional or mechanical assistance) her/his arm in the axial direction. Those movements are to promote recovery according to conventional therapy or rehabilitation emphasizing corresponding movements. In contrast, the present invention's methods, systems and apparatuses for pre-action therapy principally target brain structures, cortices, synapses and processes i.e., principal pathological sites for ABI/TBI survivors or other affected individuals, without requiring the survivor's corresponding movements.

Making corresponding physical therapy movements are variably effective, but difficult or impossible for those recovering from paretic, paralyzed and/or hemiplegic ABI/TBI or other conditions or disorders noted in this disclosure. From survivors' perspectives, the challenges and questions are how to regain physical actions or to move without (and before) being able to move. ABI/TBI survivors are left with disconnections between, on one hand, intact and in many cases, initially physically uninjured body parts and on the other hand, dysfunctional brain activity required for movements of body parts. In some cases, a survivor's difficulties are magnified due to the survivor's non-awareness of the existence of an unusable, disabled, impaired or handicapped body part. One challenge for ABI/TBI survivors is to regain the use of body parts. A technical challenge addressed with embodiments of the present invention is for users to control virtual body parts to make simulated movements and actions before, during, after or adjunctive to using physical or assistive rehabilitation or therapeutic methods that use corresponding physical actions made by such body parts. Thus, to regain full and expeditious control of using ABI/TBI-affected body parts, the present methods and apparatuses provide pre-action therapy.

Conventionally for ABI, at least one of three non-virtual-anatomical therapies can be used. These include, motor imagery; mirror therapy; and action-observation therapy. Motor imagery involves imagining motor controls and attempting to physically exercise the resulting imagery. Mirror therapy has been used for amputees experiencing phantom limb pain. It involves using an intact body part to make physical actions reflected in a physical mirror. The mirrored actions appear to be made by the contralateral (amputated) body part. The patient's observation of said actions has been shown to decrease or terminate phantom limb pain. Action-observation therapy is theoretically mirror neuron based and involves viewing physical actions followed by the patient's efforts to imitate the observed actions. Embodiments of the present invention, unlike other therapies or rehabilitation techniques, enables individuals to make, in a virtual environment, independent inputs that interactively control virtual body parts and activate attached or unattached body part devices such that the devices activate or stimulate one or more body parts to make an actual physical movement. By personally causing simulated physical actions to be simulated and thereby actual physical movements/actions to be made, users produce real visuo-motor (i.e., visuo-action) feedback from said simulated movements/actions and induce rehabilitation.

Humans excel in physical action, the result of making repeated physical actions, accompanied by feedback from such actions, resulting in improved motor actions. For unaffected individuals, the process of creating productive sensorimotor feedback derives from making actual physical actions in the real world. That process is variably unavailable or impossible for many survivors of ABI and/or the presently disclosed conditions. However, for ABI survivors the present invention may be used to create productive virtual action feedback directed to regaining and/or improving physical actions for daily living without making actual physical actions in the real world.

Aspects of the present invention relate to methods and apparatuses for pre-action therapy, also disclosed as pre-action therapy for ABI/TBI survivors. The term ABI/TBI survivors in the present disclosure includes without limitation other conditions and disorders presently disclosed and others to which pre-action therapy may be useful. More particularly, the present invention is for pre-action therapy by ABI/TBI survivors and other individuals using virtual body parts. In an aspect, a user, who may be an ABI/TBI survivor, may engage in one or more interactive pre-action activities. iP-ATA provides ABI/TBI survivors with alternative physical-action feedback. iP-ATA feedback fosters the user's restoration of pre-action motor control processing via controlled/directed, virtual body parts corresponding to at least the user's body parts that suffered reduced or lost functionality as the result of ABI or TBI. Such survivor controlled/directed, virtual body parts are caused by the user to simulate physical movements and actions thereby executing virtual-world activities as pre-action therapy for real world activities. In an additional aspect, P-AT and iP-ATA provide the ABI/TBI survivor with a pre-action therapy workout that stimulates, e.g., neuronal recruitment, interneuron communication synaptogenesis and brain plasticity.

P-AT/iP-ATA provides a method, apparatus and platform with which to link user-controlled virtual extremities to user-originated simulated physical movements. An iP-ATA can include exercises used in pre-action control/direction of virtual body parts to simulate physical movements.

According to aspects of the present disclosure, interaction with virtual body parts links the user to virtual action feedback. Furthermore, the methods and apparatuses and platform described in the present disclosure can engage ABI/TBI survivors in self-therapy for purposeful physical actions.

According to aspects of the present disclosure, an ABI/TBI survivor may target and help overcome her/his action deficits by making input controls to a system that simulates a user-controllable virtual body part, thereby directing and causing simulated actions of a movable region of the virtual body part based on the inputs, viewing feedback from such simulated actions and building new and/or rebuilding eradicated, diminished and/or impaired neurological processes.

According to the present disclosure, a user may control and direct virtual body part(s) to display simulated, human physical actions with a virtual full range of motion. The user may control a virtual body part to speed up, slow down, stop or make any combination of said actions or gradations of the same. P-AT/iP-ATA displays of virtual body part actions may be idiomatic representations of each survivor's input controls and direction. In effect, the user's virtual body part control process provides neurological stimulation for real physical movement and action processes.

In an aspect, a computer device may control the display and virtual movement of the virtual body part and may transmit one or more signals to a physical body part device, which may stimulate one or more body parts of the user to move, for example, in a way that may correspond to the movement of the user-directed virtual body part. In some examples, the physical body part device may cause body part movements by stimulating one or more receptors or triggers of the user's neurological system, which may in turn cause movement of the muscles, tendons, tissue, or any other portion of the user's body.

Furthermore, the methods and apparatuses presented herein differ from modern therapy systems, e.g., Nintendo Wii™ and Microsoft Kinect™, when implemented for physical and occupational rehabilitation and related processes. Wii™ and Kinect™ systems require users to make actual physical movements and actions that are then simulated, e.g., in virtual environments. By design and practice, Wii™ and Kinect™ users perform actual physical movements and actions that correspond to simulated actions. Conversely, the methods and apparatuses presented herein eliminate the requirement of user performance of corresponding physical actions to what are then displayed as simulated physical actions. For example, a user can make small or limited non-corresponding eye and/or head gestures carried by webcam signals and by wired or wireless transmitted brain signals, to control the simulated movements and actions of virtual body parts. In one example, any user's input signals by eye controls (alone) can direct a virtual shoulder to move an arm 90 degrees away from the body. Accordingly, a user's input controls associated with embodiments of the present invention may be non-corresponding, that is to say a user's physical method of input, e.g., eye, mouse or by wired or wireless transmitted brain signals, does not correspond to the simulated movements and actions of the virtual body parts of the present disclosure.

The inputs (controls and directions from users) described in the present disclosure may be dissociated from displayed virtual-image actions and allow ABI/TBI survivors to cause simulated physical movements and actions before and without performing real physical therapy. Each user's input according to the present disclosure may not be physical-therapy action movements of the desired movement or action. Rather, the present methods and apparatuses target without limitation neuronal systems, neural structures, gray and white matter circuitry, neurogenesis, synaptogenesis, myelination, brain plasticity and related neural processes, not necessarily any particular physical-action.

Physical therapy participation, due to its repetitive aspects, can be tedious and hindered by boredom. Participation in physical therapy is also fraught with a new injury or aggravating an old injury. P-AT/iP-ATA provide entertaining, rewarding and immersive features, including action sequence actions that result from a user's successful control, direction and manipulation of virtual body parts and objects or non-virtual robots, prostheses or exoskeleton body parts.

For example, in terms of non-limiting and non-exclusive variations of practical application, as well as research and investigation, monitoring brain activity can enhance pre-action therapy value. By using standard, readily available equipment, ABI/TBI survivors' brain activities or processes can be measured through any brain imaging technology or by analyzing blood and/or other body fluids, or biomarkers, or other substances for particular bio-chemicals, markers and/or compounds related to without limitation overall neural activity. ABI/TBI survivors' baseline neural activities or processes could be determined before, during and after pre-action therapy to measure changes accompanying pre-action therapy. Additionally, ABI/TBI survivors' brain activities or processes can be compared to non-ABI/TBI affected individuals undergoing or who underwent pre-action therapy activities to determine whether pre-action therapy is stimulating the same or similar affected parts of the ABI/TBI survivors' brains as are stimulated in the non-ABI/TBI affected individuals' brains. An iP-ATA program can be adjusted accordingly to enhance the neural activity or processes in the identified neural structures, processes or circuitry of the ABI/TBI survivors to match brain activities (including substance quantities, levels and the like) of non-affected individuals' brain structures, processes or circuitry accompanying iP-ATA. Other non-limiting and non-exclusive variations on the process, e.g., providing haptic feedback and other types of sensory feedback to a user during a P-AT-based session, are discussed in the present disclosure.

P-AT/iP-ATA can also be used as diagnostic tools. Some ABI/TBI survivors suffer mild brain injury and current diagnostics are limited to mostly subjective tests combined with some technical means. Additionally, while moderate to severe ABI/TBI is detectable through changes in brain morphology by CT-scans, MRI or other imaging technologies, mild ABI/TBI is difficult to detect or diagnose. Any survivor, who does not show severe or moderate ABI/TBI, could be introduced to iP-ATA to monitor for mild ABI/TBI. Mildly affected patients would engage iP-ATA and her/his brain activities would be compared to unaffected individuals' baseline brain activities to determine the comparative state or extent of mild injury or the possibility of unlikely or undetectable injury. P-AT may be used for assessing other levels of ABI/TBI, either solo or in conjunction with other methods or devices.

Various aspects are now described with reference to the drawings. In the following description, for purposes of explanation, numerous specific details are set forth in order to provide a thorough understanding of one or more aspects. It may be evident however, that such aspect(s) may be practiced without these specific details. Turning to FIG. 1, a system 100 for presentation and manipulation of a virtual body part as a means for pre-action therapy by a user is shown. In an aspect, system 100 may include a computing device 102, an input device 104, a display device 106 and a user measurement device 108. As used herein, the term "display device" can include any instrument for providing a physical or virtual view or demonstration of a simulation, image or model and without limitation can include display devices (e.g., monitors, televisions, touch screens, etc.), robots, machine models and/or other physical or virtual representations. Additionally, system 100 may include a body part device 128 and/or a feedback device 130. According to an aspect, computing device 102 may include, e.g., a digital computing device configured to receive and process one or more user inputs 110 from input device 104, one or more user characteristics 112 from user measurement device 108, and may generate and transmit one or more displayed images and control messages 114 to display device 106. In addition, computing device 102 may be configured to execute manipulation of a simulated virtual body part based on at least the inputs of user 120.

Furthermore, computing device 102 may include a processing engine 116, which may be configured to receive, process and transmit signals associated with the simulation, control and/or behavior of a virtual body part. The movement of the virtual body part is effected by the movement manager 126. Additionally, computing device 102 may include a memory 118, which may be configured to store user characteristics (such as neurological or chemical characteristic values observed and/or measured from a user 120) and/or instructions for executing one or more iP-ATA.

System 100 can simulate action and pre-action therapy based on movements of a first demonstrative virtual object image on display device 106 and at least one input device 104 for providing an input to system 100 to controlling at least one additional user-controllable virtual object image or virtual body part. In an example, display device 106 of system 100 can simulate the demonstrative virtual object or body part making an exemplary movement, task or skill associated with the demonstrative virtual object. The user may then, without limitation, use a physical, virtually representative or brain signaling device (e.g., in the form of input device 104) that may (or may not) correspond to the demonstrative virtual object in physical composition to emulate/mimic or oppose the exemplary movement, task or skill of the first demonstrative virtual object image on display device 106.

Furthermore, display device 106 may be configured to simulate one or more virtual body parts and actions of the simulated virtual body part(s). In an aspect, display device 106 may simulate a virtual body part visually on a screen or display, such as, but not limited to, a computer monitor, projector, television, or the like). The virtual body part(s) on display device 106 can be affected and/or controlled by user inputs from input device 104, and thus may be a "user controllable" virtual body part. Virtual body part(s) on display device 106 may carry out simulated human anatomical movements which represent a simulated, physically achievable anatomical movement and/or action in response to signals encoded in inputs 110. Further, the movements, actions, animations, etc. performed with the virtual body part(s) on display device 106 can be distinct from the physical aspects of actions performed by user 120 to generate inputs 110 with input device 104.

Display device 106, in addition to displaying model and user-controllable virtual body parts, can display other information related to physical and neural therapy. As user 120 manipulates virtual body parts through input device 104, display device 106 can simultaneously or alternatively display statistics related to the performance of user 120. For example, computing device 102 can calculate statistics related to a user's proficiency in one or more iP-AT/iP-ATAAs and display these statistics on display device 106. In embodiments where more than one user 120 interacts with system 100, statistics for each user can be calculated and compared by computing device 102 and shown with display device 106. In addition, display device 106 can allow user 120 to view video (e.g., previous emulation, mimicking of particular movements and gestures) to observe correct and/or incorrect movements as controlled by user 120 through input device 104. In some examples, computing device 102 can generate a video representation of a previous input controlled movement, shown on display device 106 in a "play" or "playback" mode. The video generated with computing device 102 can be displayed in a first-person perspective, a third-person perspective, or any other playback perspective currently known or later developed. In addition, user 120 can view video of system 100 being operated by another user (not shown) of system 100, either previously or simultaneously. In a further addition (also not shown) displayed video may be accompanied by audio and/or closed captioned; just as recorded or generated audio can be presented with, without or instead of accompanying video and/or displayed messages.

In an aspect, input device 104 may be configured to receive one or more physical or non-physical inputs 122 from user 120 to translate, process and forward the translated and/or processed inputs to computing device 102 as inputs 110. Although a single user 120 is shown by way of example in FIG. 1, it is understood that an input device or a plurality of input devices 104 can receive physical or non-physical inputs 122 from a user or a plurality of users 120 for each system or a plurality of systems 100. Thus, computing device 102 can receive cooperative and/or competing physical and/or non-physical inputs 122 from simultaneous and/or sequential, cooperative and/or competing users 120, and display single or multiple simulated human anatomical movements of single or multiple virtual body parts. In an aspect, input device 104 may be any means of receiving direct physical or non-physical input from a user 120, such as, but not limited to a keyboard, mouse, touch pad, smart phone, laptop, computer, motion control system, gesture sensor, brain computer interface, etc., which may or may not include a representation of a physical tool, instrument, etc., a sensory body harness, or generic computing device, an input device that senses input without intervention of the user, etc. In addition, it is understood that user 120 can represent several users, each participating in a competitive, cooperative, simultaneous and/or sequential fashion. Thus, embodiments of the present disclosure contemplate multiple users each engaging in therapy with a single computing device 102 or with multiple computing devices 102.

Alternatively or additionally, input device 104 may be a device configured to generate input 110 by recognizing and processing one or more user actions via user action recognizing component 124. For example, in an aspect, user action recognizing component 124 may be configured to recognize user inputs via, e.g., non-limiting example, eye action, nominal physical action of hands or other body parts, blinking, nodding, vocal control and/or by detecting and monitoring neurological signals generated by the user's body. For example, user action recognizing component 124 may include a component capable of reading instructions signaled in the brain, spinal cord, or any other neurological circuit or tissue of user 120. In an embodiment, user action recognizing component 124 of input device 104 can include an electroencephalography ("EEG") device or a similar device that reads and interprets brain signals generated by the user and transmits brain signals to system 102. Furthermore, the signals from any form of input device 104 (including, without limitation, said EEG device) may be transmitted as input 110 to computing device 102 via any means of transmission, including Bluetooth™ wireless data exchange methods or other wireless or wired communication methods or standards.

Alternatively or additionally, a body part device 128 may receive one or more external body part control signals 132, which may cause body part device 128 to move, for example, by mechanical means. In an aspect, body part device 128 may be, but is not limited to being, a robotic arm, shoulder, or the like. In some examples, the body part device 128 may stand alone and be placed in a location viewable by user 120. Additionally, the external body part device may be attached to user 120, which may allow the user to witness real-time or substantially "true to life" actions associated with his or her physical inputs 122.

In an additional or alternative aspect, body part device 128 may be configured to receive one or more control signals from computing device 102 corresponding to the virtual movement of the virtual body part being manipulated by the user. Based on the one or more control signals, the body part device 128 may process the control signals and stimulate one or more target body parts 150 of user 120 (or of a non-user (not shown)) to prompt movement of one or more body parts, which may include target body part 150.

In yet another aspect, system 100 may include a feedback device 130 configured to provide feedforward and/or feedback (collectively, "sensory response 136") to user 120 (and/or intervening devices in alternative embodiments), which optionally can be provided directly to target body part 150 along the corresponding phantom line in FIG. 1. In an aspect, feedback device 130 may receive one or more feedback control messages 134 related to the feedback device from computing device 102, which may govern the action and behavior of the feedback device 130. In an aspect, feedback device 130 may be configured to generate, by non-limiting example, force feedback, pneumatic feedback, auditory or visual feedback, non-force feedback, or any other form of feedforward and/or feedback that may indicate an output of computing device 102 related to pre-action therapy. For example, feedback device 130 may include a sensory response unit 138, which can be in the form of, e.g., a mechanical device that a user may attach to his or her hand or arm that may provide force feedback to the user's hand or arm in order to bend the user's wrist. In such an example, this bending may occur where the user selects a virtual wrist on display device 106 and moves the virtual wrist up and down (or in any direction) by moving input device 104. Based on this input, processing engine 116 may generate and transmit a feedback control message 134 to feedback device 130 which may provide a force to the user's body part (e.g., a wrist) to move the body part substantially in unison with the action of the virtual image, which may or may not be shown on display device 106 concurrently.

Further, the present disclosure contemplates a variety of methods and devices for providing feedback from feedback device 130, allowing users to learn and practice an exemplary movement, task or skill based on displayed demonstrative actions, including physically achievable simulated human anatomical movements, with one or more virtual body parts. Output from feedback device 130 may include haptic feedback, also known in the art as "tactile feedback," or may also include other types of feedback (e.g., auditory feedback). Haptic feedback may include feedback to a device that is secured to, held by, or manipulated by a user to provide actual forced movement of target body part 150 (e.g., an electrically actuated, computer controlled harness, arm strap, etc., that may force the hand and/or arm to extend or retract at the elbow) or sensory/tactile feedback (e.g., a user's mouse or trowel or other physical object that e.g., can vibrate, pulse and/or provide varying temperature sensations to user 120). Computing device 102 can control the feedback provided with feedback device 130 to excite neurons in a prefrontal cortex, premotor cortex, supplementary motor area, etc. of user 120. As discussed elsewhere herein, premotor action planning by user 120 can be affected by visual and tactile stimulation. Thus, sensory feedback provided with feedback device 130 can be customized to mentally stimulate user 120 in different ways to accommodate varying needs and situations. Computing device 102 can also control the extent of sensory feedback provided by feedback device 130 through program code. The degree of sensory feedback sensations provided to user 120 can be derived by computing device 102 by comparing input controlled movement 110 against a "model movement," which can represent a model simulated human anatomical movement. The model simulated human anatomical movement can be stored on computing device 102 (e.g., in memory 118) or on an external computing device or processing system. Thus, user 120 can receive feedback through feedback device 130 which indicates his or her degree of success in imitating or opposing the model simulated human anatomical movement.

Aspects of system 100 according to the present disclosure can include a demonstrative virtual object image, e.g., a virtual body part, being displayed on display device 106. The demonstrative virtual object image can demonstrate a model simulated human anatomical movement, or other simulated action or gesture, before, during, or after the time that user 120 provides physical or non-physical inputs 122 to input device 104. Computing device 102 can define feedback control messages 134 based on the accuracy or correctness of input controlled movements as compared to the model simulated human anatomical movement, action, or gesture performed with the demonstrative virtual object image.

In an embodiment, input device 104 and feedback device 130 can be part of a user interface device 160 (shown in phantom). User interface device 160 can integrate input and feedback aspects of system 100 to centralize the physical and neural therapy experience of user 120. In an embodiment, user interface device 160 can include a computer mouse with sensory response units 138 installed therein. Thus, user interface device 160 can enhance the therapy of user 120 by providing immediate feedback, as user interface device 160 can be a single component for interacting with computing device 102 to communicate inputs 110 and receive feedback control messages 134.

User interface device 160, including input device 104 and feedback device 130, can take many other forms. For example, input device 104 may include a motion-based controller system similar to those found in the Nintendo Wii™ or Microsoft Kinect™. In addition or alternatively, a biomedical sensor glove, e.g., a glove device according to the ArmAssist™ system developed at McGill University, Canada, can be used for input device 104, body part device 128 and/or feedback device 130. In other example embodiments, input device 104, feedback device 130 and/or user interface device 160 can include, e.g., a real or representative: baseball glove or bat or hockey stick with vibration capability; a trowel with force-feedback or vibration capability; or any other object used in any trade or profession (e.g., without limitation, a scalpel for surgery, pen, pencil or brush for drawing, a diamond cutting tool) or sport movements involving pre-action and action therapy or the like. Further, input device 104 can be configured to detect a user's brain signal (e.g., an electrical or neurological signal), and provide input 110 based on detecting the user's brain signal. For example, input device 104 may be any currently known or later developed device configured to identify whether a particular brain activity of user 120 occurs, and transmit input 110 to computing device 102 based on identifying that the particular brain activity is occurring in the present, or has previously occurred. Other embodiments of the present disclosure can include an industrial therapy system (e.g., metalworking or welding) or skill therapy system (e.g., culinary therapy) which allows user 120 to engage in pre-action therapy with an embodiment of system 100 before being introduced to traditional physical and occupational therapy methods that may be more expensive, dangerous, or error prone.

In an additional aspect, system 100 may include a user measurement device 108, which may be configured to measure one or more user characteristic values before, during, and/or after engaging in pre-action therapy activities. In some examples, user characteristic values may include without limitation neurological or chemical data, pulse, blood pressure, or any other measurable characteristic or physical parameter of an animal, which may include a human being. In an aspect, user measurement device may use imaging technology to measure these user characteristics, and such imaging technologies may include, without limitation, Magnetic Resonance Imaging ("MRI"), Functional Magnetic Resonance Imaging ("fMRI"), Computed Tomography ("CT"), Positron Emission Tomography ("PET"), Electroencephalography ("EEG"), Magnetoencephalography ("MEG"), Multi-Voxel Pattern Analysis ("MVPA"), Near-InfraRed Spectroscopy ("NIRS"), and High Density Fiber Tracking ("HDFT"). Thus, user measurement device 108 can include a component or group of components which function as a neuronal activity monitoring device in communication with computing device 102, which can allow computing device 102 to monitor the neuronal and/or brain activity of user 120. Activity sensed with user measurement device 108 can affect the display or demonstration of simulated body parts, movements, etc., by computing device 102 in an iP-ATA. In particular, program code for a given iP-ATA may include commands to adjust the display of actions, gestures, movements, etc., to improve the proficiency and accuracy of user 120. In some embodiments, settings adjustments within a particular iP-ATA may occur in real time based on continuous input from user 120 simultaneously with the operation of input device 104 and feedback device 130.

In a further aspect, user measurement device 108 may send the measured user characteristic data 112 to computing device 102 upon measurement. The user characteristic data may be stored in memory 118 for later use or fed to processing engine 116 as feedback data that processing engine 116 may use to alter an ongoing pre-action therapy activity, such as an ongoing iP-ATA, or may be used to diagnose a medical condition. Alternatively, where the user characteristic data is stored in memory 118, such data may be used to tailor future iP-ATA to the user's individual characteristics and/or current skill level and/or to track the progress of a user over time and/or to improve P-AT/iP-ATA.

Another aspect of system 100 can include a computer-controlled restraint therapy device 152 (alternatively identified as a "restraining device") optionally mechanically coupled between feedback device 130 and user 120 and/or target body part 150. Restraint therapy device 152 can force particular body parts, extremities, etc., of user 120 (and/or target body part 150, as shown by the corresponding phantom line in FIG. 1) to remain in place during physical and/or neural therapy to improve the feedback and therapy of particular body parts. Restraint therapy device 152 can be in the form of single or multiple restraint therapy devices 152, which can be added and removed as desired to customize the therapy of user 120. In an embodiment, restraint therapy device 152 can include one or more devices configured to restrain up to and including all bodily extremities of user 120. As an example, where user 120 may desire therapy in only one arm, computing device 102, optionally through feedback device 130, can dispatch a signal 154 (shown in phantom) to restrain at least one extremity of user 120. The restrained extremity can be the extremity to be trained (e.g., to mandate particular types of motion), or an extremity which is not trained (e.g., to prevent other body parts from moving).

Figure 2:
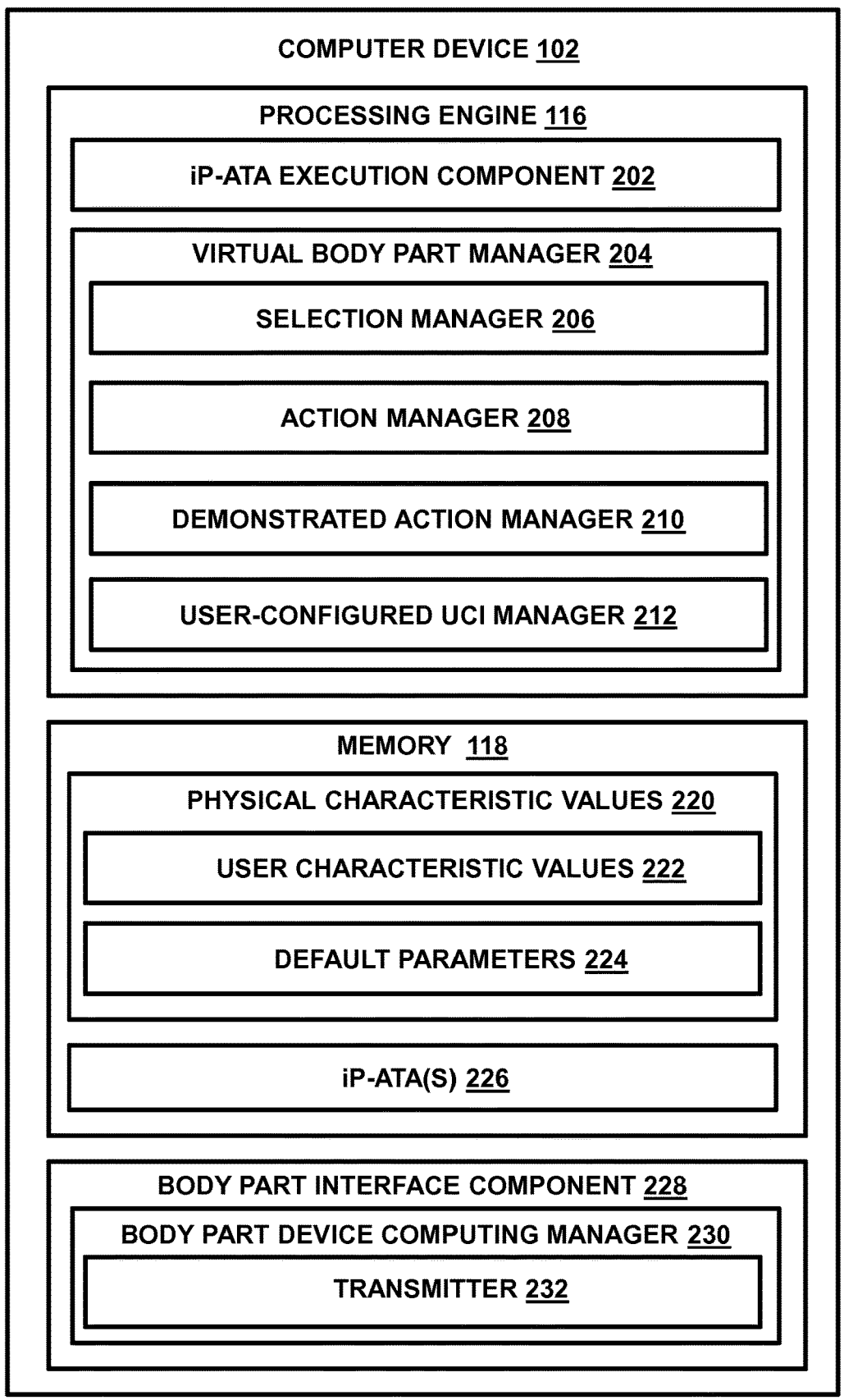
FIG. 2 depicts a component block diagram of a computer device according to embodiments of the present disclosure.

Turning to FIG. 2, an illustration of components comprising computing device 102 (FIG. 1) is provided. In operation, computing device 102 may present an initial or default virtual body part to a user, for example, when the user, therapist, or any other type of user initially boots up computing device 102, selects an iP-ATA. To display this default virtual body part, virtual body part manager 204 may query memory 118 for default parameters 224 of a set of physical characteristic values 220 stored thereon and may process and display the default virtual body part by sending, for example, one or more display images and messages to a display device 106. In addition, once the user begins a P-AT session, computing device 102 may receive inputs from the user, such as, but not limited to, selection inputs and action inputs. Based on these one or more inputs and pre-stored and executable iP-ATA 226 located in memory 118, the computer device may present a selectable, movable, and otherwise interactive virtual body part with which a user may engage in iP-ATA.

As outlined herein, computing device 102 may include processing engine 116 and memory 118, the operation and composition of which are explained in reference to FIG. 2. First, processing engine 116 may be configured to process one or more input signals and transmit the processed signals to a display device 106 for presentation of a user-controllable image, such as a virtual body part, to a user 120. For purposes of the present description, a user-controllable image ("UCI") may be all or part of a virtual body part or object controllable by user input to simulate physical movements and/or actions, wherein these physical movements and/or actions are non-corresponding to the user's physical movements/actions in performing the user input. Examples of UCIs described herein may include a virtual body part or virtual body parts, or virtual body parts and objects, but the scope of such examples should not be limited thereto.

In an aspect, processing engine 116 may include an iP-ATA execution component 202, which may process user inputs to generate display control messages according to instructions related to one or more iP-ATA. In a non-limiting example, a user may select a particular iP-ATA in which to engage and as a result, iP-ATA execution component 202 may load the iP-ATA instructions from iP-ATA 226 stored in memory 118. After loading the iP-ATA execution component 202 may generate one or more display control images and messages for transmission to a display device 106 based on the iP-ATA and any inputs received from any input device. Furthermore, in an aspect, iP-ATA execution component 202 may be configured to alter one or more iP-ATA instances based on feedback from a user measurement device. In a non-limiting example, iP-ATA execution component 202 may receive an indication that a user's neurological system is weaker or stronger than in the past and may make engaging in a particular iP-ATA easier or more difficult to provide further neurological improvement.

In an additional aspect, processing engine 116 may include a virtual body part manager 204, which may be configured to virtually construct and manage action of a virtual body part, including a virtual human body part, that computing device 102 may generate for simulation on a display device. Furthermore, for purposes of the present description, the term "display device" may correspond to display device 106, body part device 128, feedback device 130, or any other device or means capable of producing output corresponding to an action, and/or status of a virtual body part, including output resulting from user input during iP-ATA.

In an aspect, virtual body part manager 204 may include a selection managing component 206, which may be configured to receive one or more selection inputs from a user or an input device manipulated by a user, wherein the selection inputs may correspond to a user selecting a virtual body part or a portion thereof. Furthermore, based on a selection input, selection manager 206 may map a select location associated with a selection input to a virtual body part or a portion thereof, which may correspond to a virtual body part selected for subsequent or concurrent action by the user.

Furthermore, virtual body part manager 204 may include an action manager 208, which may be configured to receive one or more action inputs from a user and generate one or more display control signals that cause displayed action of the virtual body part. In an aspect, this displayed action may correspond to the virtual body part or portion thereof selected by the user and mapped by selection manager 206. Additionally, action manager component 208 may generate and display the action based on the user "dragging," "pointing," "tapping," "touching," or otherwise correctly manipulating at least a portion of the movable body part.

Furthermore, action manager component 208 may base its virtual body part action generation and/or other processing actions on a particular iP-ATA, which may have been pre-selected by a user and loaded for execution by processing engine 116. In an aspect, an action input may be input by a user and received by computing device 102 as a result of the user partaking in such an iP-ATA or any other pre-action therapy activity. Additionally, in an aspect of the present disclosure, a user input action may be physically non-corresponding to the desired or eventual action of the simulated virtual body part with which the user is interacting. For purposes of the present disclosure, a non-corresponding action may be a user action that differs relatively significantly from a simulated action. For example, a user engaged in a pre-action therapy activity may wish to move a virtual forearm directly upward using a mouse as an input device. To do so, according to aspects of the disclosure, the user may first navigate a cursor and click a mouse button to select the virtual forearm on a display device, thereby inputting a selection input. Next, the user may keep the cursor on the virtual forearm and may hold a mouse button down to signal a beginning of an action input. Thereafter, the user may drag the mouse two inches along a mouse pad, with the mouse button held down, and may observe the virtual forearm rise upward, for example, from a virtual hip area to a virtual head area. To carry out this action, the user's hand or forearm may have moved approximately two inches in a direction parallel to the mouse pad, but resulted in a virtual action of the virtual forearm that was upward in direction and appeared greater than two inches in magnitude. Therefore, this example user input action is non-corresponding to the action of the virtual body part.

Additionally, virtual body part manager 204 may include a demonstrative action manager 210, which may be configured to provide display control messages to a display device to make a demonstrative action of the virtual body part. For example, demonstrative action manager 210 may store and/or execute a retrieved demonstrative action to be displayed to the user as a "ghost" action. In an aspect, the user may view the demonstrative action and may then attempt to manipulate the virtual body part to mimic or oppose the demonstrative or ghost action.

Furthermore, virtual body part manager 204 may include a user-configured UCI manager 212, which may tailor or otherwise configure a simulated virtual body part to a user's body and/or alter the behavior of the simulated virtual body part based on one or more user characteristic values 222. In an aspect, such characteristics may include anatomical and physiological data characteristic values associated with the user, such as without limitation height, weight, arm length, muscle mass, ABI/TBI-affected body parts, handedness, age, gender, eye/hair/skin color and the like. In additional or alternative aspects, the user characteristics may include historical iP-ATA performance data associated with the user, current neurological or chemical measurement characteristics or parameter values, or the like.

In an aspect, user-configured UCI manager 212 may obtain these user characteristic values 222 from memory 118. Alternatively, user-configured UCI manager 212 may obtain these user characteristic values from a source external to memory 118, such as, but not limited to, a user measurement device configured to measure neurological and/or chemical characteristics of the user during pre-action therapy activities, by querying a user or the user's trainer, doctor, coach, therapist or rehabilitation specialist for such characteristic values and receiving a characteristic value input in response, or otherwise receiving user-specific performance, anatomical, physiological, or other characteristic values. In another example implementation, UCI manager 212 can obtain user characteristic values 222 from user measurement device 108 shown in FIG. 1 and discussed earlier.

In addition, user-configured UCI manager 212 may be configured to compare the user characteristic values, or user parameters, to one or more default parameters 224 stored in memory 118. In an aspect, default parameters 224 may comprise the parameters of a default virtual body part of the present disclosure, and may include anatomical and physiological data (e.g., handedness, strength and bone length, limitations on range of motion, skin characteristics and the like). Such characteristics may conform to the behavior and attributes of the default virtual body part displayed to a user before tailoring, configuring, or otherwise customizing the virtual body part to the user. In order to perform such customization, the user-configured UCI manager 212 may compare the obtained user characteristic values (e.g., user characteristic values 222) to default parameters 224. In an aspect, where the comparing determines that a user characteristic value differs from the default parameter value for a characteristic, the user-configured UCI manager may set the compared parameter of the virtual body part to be displayed to the user's characteristic value. Alternatively, where an obtained user characteristic value does not differ from the default parameter, user-configured UCI manager 212 may leave the compared parameter unchanged.

In an additional aspect, processing engine 116 may be configured to generate and/or transmit one or more display control signals to the display device to make action of the virtual body part. Furthermore, processing engine 116 may be additionally configured to calculate and/or report an action degree or action magnitude associated with an action of the virtual body part. In an aspect, processing engine 116 may display the calculated action degree or action magnitude by generating one or more display control messages, which may be generated and transmitted in substantially real time, for transmission to a display device for visual indication of the action degree to the user.

Furthermore, computing device 102 may include a memory 118, which may be configured to store information for use by other components in a system, e.g., processing engine 116. Such information may include physical characteristic values 220, which may include user characteristic values 222 associated with one or more users and/or default parameters 224 associated with a baseline or default UCI, such as a virtual body part. Furthermore, memory 118 may store neurological, chemical, or any other data related to a user's body (e.g., without limitation neurological signaling data or maps, neuron activity data, etc.) generated and/or observed by a user measurement device before, during and/or after a user engaging in pre-action therapy. Such data may also be fed back to processing engine 116, which may alter a current or future iP-ATA based on the feedback.

In an additional aspect, such user data may be used to diagnose one or more medical conditions. For example, computing device 102 may output the user data to a physician or other professional, who may analyze the data and diagnose the medical condition. In an alternative or additional and non-limiting example, computing device 102 may contain instructions executable by processing engine 116 to automatically diagnose a medical condition based on the user data stored on memory 118.

In addition, memory 118 may include executable instructions (e.g., executed by processing engine 116), that when performed, allow the user to engage in one or more pre-action therapy activities. As used herein, pre-action therapy activities may include interactive electronic therapy or activities, such as, but not limited to, iP-ATA 226. The iP-ATA 226 may govern the behavior of a virtual body part in response to one or more inputs by a user during pre-action therapy activities.

Additionally, executive motor functions by user 120 are involved in all iP-ATA. According to some example iP-ATA, virtual upper body parts are presented to users to control in order to simulate purposeful physical actions—for example, opening and closing a virtual hand. Some iP-ATA may be virtual task therapy, which may couple engaging control of virtual body parts and objects to accomplish tasks and/or solve problems—for example, dropping a spoon into a cup.

Furthermore, upper extremity exercises of some non-limiting examples, a iP-ATA may include engaging control of any part or all of an affected hand, lower or upper arm (right or left), executing flexion/extension, supination/pronation, abduction/adduction, or any other extremity or body part action in any direction. According to the iP-ATA contemplated herein, users can manage displays of some of, the majority of, or all of a virtual upper extremity from substantially any angle. Additionally, the virtual body part may comprise fingers or toes, which may be manipulated individually or in combination. The virtual body part may comprise a wrist, which may be flexed/extended, abducted/adducted, or supinated/pronated. Furthermore, according to some example iP-ATA, the virtual body part may comprise an arm, wherein the lower and upper arm may be manipulated independently or in combined action of all joints of the arm, wrist and hand.

In some example iP-ATA where the virtual body part is a virtual hand, example therapy for pre-action therapy may include:

Pincer action to grasp a key.

Two finger action to grasp a ball and drop it into a cup.

Multi-finger action to pick up a spoon and drop it into a cup.

Full hand grasp around a mug handle.

Tapping actions by index and middle fingers on a remote controller.

Hand grasps of objects shaped as stars, circles or squares, then placement in similarly shaped slots.

Regarding virtual arms in some non-limiting example iP-ATA where the virtual body part includes a virtual arm and/or a virtual hand, example therapy for pre-action therapy may include:

Opening a correct box, i.e., selecting and opening the correct numbered and colored box (e.g., box 24 purple) in a circle of nine numbered and colored boxes, after observations and computations as elementary as choosing the (single) "lowest purple box bearing an even number" (purple 24 is correct) to computations based on several numbered boxes, e.g., "choose the highest blue even numbered box, subtract the second of its numbers from the first, square it and find the green box with that result" (if 92 blue is selected the subtraction yields number 7, which when squared is 49, so green box 49 is correct). Nine box open action, as above, with voice instructions to the user.

Similar open the box action in a more elementary vertical presentation of five boxes.

Light bulb action requiring the user to unscrew a light bulb, choose the correct lettered socket and screw the bulb into the correct socket.

Engaging card therapy, for example in a simple action the virtual arm and hand are controlled to select a pair of deuces, place that pair, right side up on a surface, then the user must choose the lowest numbered pair that wins over a pair of deuces, alternately the highest numbered pair that wins over deuces, then the lowest (or highest) pair of picture cards that wins over deuces and so forth, to more complex combinations of engaging cards/hands.

Puzzle therapy in which the cursor is used to move some number of puzzle pieces to assemble a complete representation of any display noted above. For example, a hand image, in any orientation, position and configuration may be disassembled by the puzzle action into puzzle pieces to be reassembled by the user, or a more complex disassembly of the nine box arm action may be "puzzled."

Simple number action displaying 0-9 and processes (add, subtract, multiply, divide and equals sign) and calling for the iP-ATA user to use a virtual arm and hand to select numbers and processes and to make any number of computations by arraying the numbers and processes accurately.

Simple letter action engaging any or all letters of the alphabet and calling for the iP-ATA user to use a virtual arm and hand to select letters to make any number of words by arraying the letters accurately.

Where the virtual body part is at least one virtual muscle, pre-action therapy may include selection of said at least one virtual muscle to cause it to contract or relax at any rate of speed or to stop, for example, to end cramping or focal cervical dystonia or to regain movement impeded by hand dystonia. Therefore by loading and/or executing the one or more stored iP-ATA 226 of memory 118, computing device 102 may present a user with a UCI, such as a virtual body part, with which the user may interact to participate in pre-action therapy activities.

In a further aspect, computing device 102 may include a body part device interface component 228, which may be configured to interface with an external (or integral) body part device (e.g., body part device 128 (FIG. 1)), generate one or more control signals based on the user control of the virtual body part, or UCI, and transmit the one or more control signals to the body part device 128 for eventual stimulation of a target body part 150. In some examples, body part device interface component 228 may include a body part device computing manager 230 which may generate the one or more control signals based on the user control of the virtual body part. In a further aspect, body part device computing manager 230 may include a transmitter 232, which may be communicatively coupled to body part device 128 via a communicative connection, and may be configured to transmit the one or more control signals to body part device 128. In some examples, transmitter 232 may transmit the signals wirelessly or via a transmission medium, depending on whether computing device 102 is tethered to body part device 128 via a transmission medium, such as a bus or other wire. For example, where computing device 102 is connected to body part device 128, transmitter 232 may be configured to transmit the control signals over the transmission medium (though it may also transmit the control signals wirelessly as well). Alternatively, where the computing device 102 is not tethered to the body part device, transmitter 232 may transmit the one or more control signals wirelessly. As such, transmitter 232 may include one or more antennas or transceivers.

Figure 3:
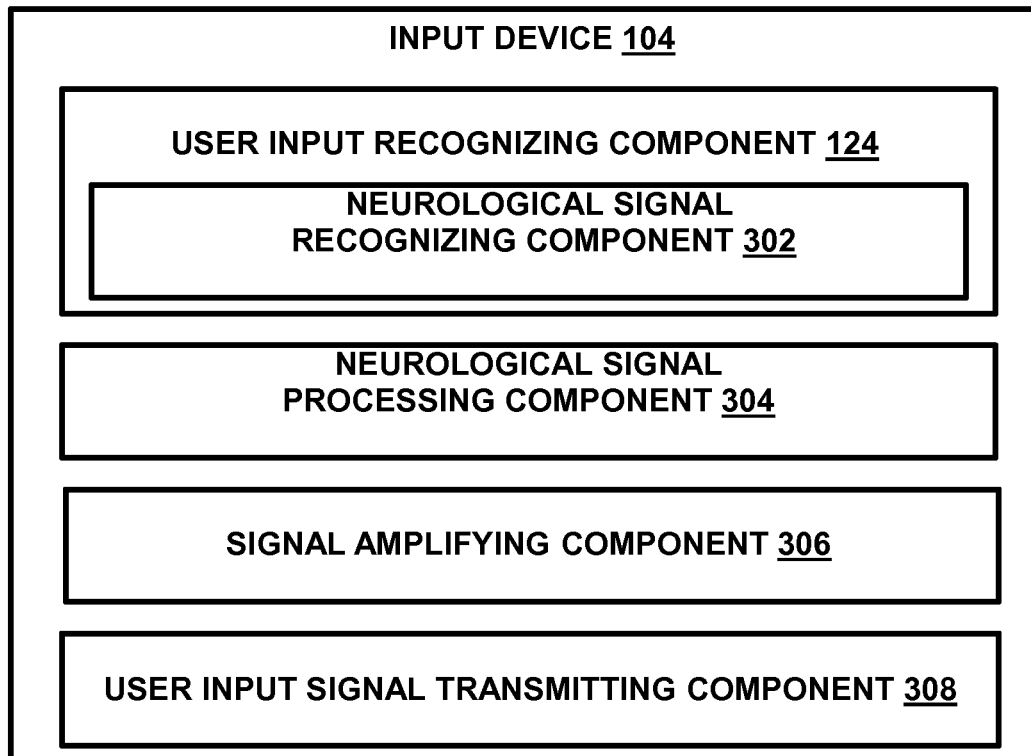
FIG. 3 depicts a component block diagram of an input device according to an embodiment of the present disclosure.

FIG. 3 illustrates an example input device 104 for recognizing one or more physical or neurological signals of a user, processing said signals, and transmitting a related signal to a computer device as an input. Besides standard mouse-like devices, in some examples, input device 104 may include a brain-computer interface ("BCI"), mind-machine interface ("MMI"), direct neural interface, or a brain-machine interface ("BMI"), or any other interface, neurological signal detection device, or component known to one of ordinary skill in the art capable of providing input to a computer device based on neurological signaling. In some examples, neurological signals may be received or detected from a user's brain, a user's spinal cord, or any other neurological pathway in the user's body, e.g., with user measurement device 108 (FIG. 1). Furthermore, input device 104 may include a headset or other external device that is configured to be affixed to a user's body, such as to the user's head, torso, back, arm, hand, foot, knee, leg, foot, toe, finger, such that neurological signals may be received by one or more sensors attached to the external device.

Additionally, in an aspect, input device 104 may include a user action recognizing component 124. In some examples, user action recognizing component 124 may include a neurological signal recognizing component 302, which may be configured to recognize or detect, for example, invasively or non-invasively neurological signals that may be used to control a virtual image and/or a related body part device to move based on the neurological signals. For example, neurological signal recognizing component 302 may comprise one or more neurological signal sensors, such as neural sensors or other brain-wave sensors known to one of ordinary skill in the art. In an aspect, these sensors may be affixed directly to the user or a body part thereof, such as the brain, the spinal cord, or the like, or may be located proximately close to the user or the body part (e.g., above the skin or hair), such that the sensors may recognize or sense the neurological signal by non-invasive means.

Furthermore, input device 104 may include a neurological signal processing component 304, which may be configured to process a recognized or detected neurological signal, including signal filtering and noise reduction. For example, in an aspect, the neurological signal processing component 304 may be configured to correlate neurological signal to movement of one or more virtual images, virtual body parts, cursors, or other displayed objects being observed by the user. For example, in a non-limiting example, where a virtual hand is observed by the user on a display, the user may attempt to select a portion of the virtual hand, such as a finger, and move the finger in a flexor (or other) motion. This attempt to select and/or move the portion of the virtual hand may cause the user's brain and associated neurological circuitry to produce neurological signals corresponding to signals that would move a corresponding portion of the user's hand, which, in some aspects, may no longer be present on the user's body. However, the neural pathways associated with such hand movement may still be present in the user's brain and body. The neurological signal processing component may process these neurological signals to correlate to an associated virtual movement of the virtual image being simulated. Alternatively, the neurological signal may be non-corresponding to actual movement of the no-longer-present body part but may instead be related to neural selection of a displayed cursor. For example, the user may envision the cursor in the user's brain and use mental processes to move the cursor to a virtual body part, select the body part through a mental selection process, and move the body part (e.g., a flexor movement of a displayed virtual finger).

Such processing by neurological signal processing component 304 may comprise executing, via one or more processors, one or more instructions stored on a computer-readable medium. In an aspect, neurological signals (e.g., those recognized by user action recognizing component 124 or neurological signal recognizing component 302) may be correlated to one or more control signals for altering the virtual image (e.g., selection, movement, etc.) by means of a formula, algorithm or flow of mathematical operations, look-up table, or other stored correlation information.

In a further aspect, to allow sufficient signal strength to interface with a computer device (e.g., computing device 102 (FIG. 1)), input device 104 may include a signal amplifying component 306, which may be configured to amplify the voltage of neurological signals (e.g., electrical signals measured with or output from an EEG device) to levels that may be input to the computer device as user input signals. In an aspect, signal amplifying component 306 may comprise one or more digital or analog amplifiers known to those of ordinary skill in the art. Furthermore, input device 104 may include a user input signal transmitting component 308, which may be configured to transmit the processed and amplified neurological signals, or user input signals, to one or more computer devices to effectuate virtual or non-virtual movement of a virtual or non-virtual body part. In some examples, user input signal transmitting component 308 may include a wired or wireless transmitter or transceiver and may include one or more transmission antennae and related circuitry.

Figure 4:
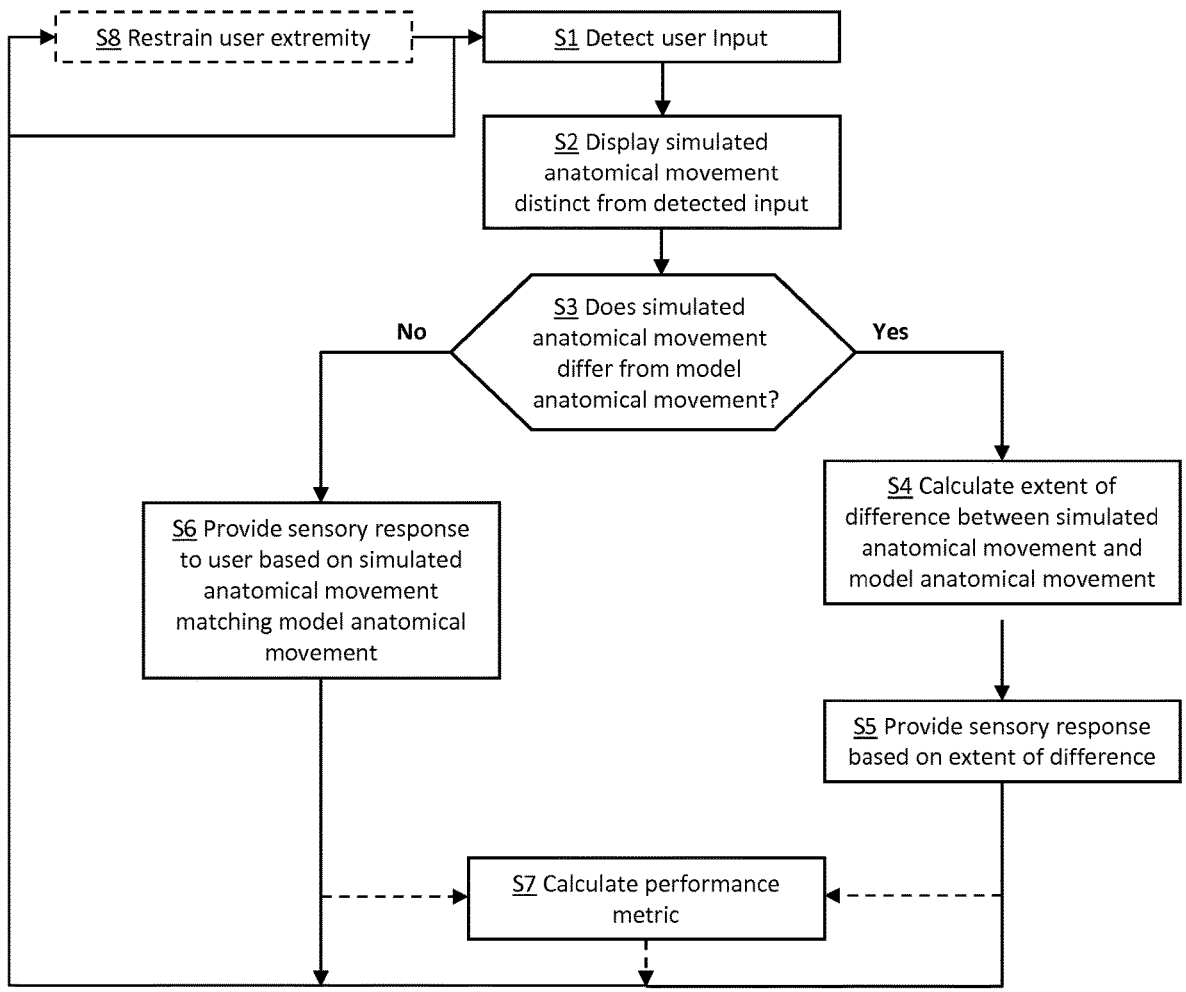
FIG. 4 depicts a process flow diagram illustrating a method according to an embodiment of the present disclosure.

Turning to FIG. 4, a flow diagram illustrating a method of physical, pre-action and related neural therapy according to an embodiment of the present disclosure is shown. In step S1, system 100 (FIG. 1) can detect an input from a user for controlling a simulated human anatomical movement. The input detected in step S1 can be in the form of an action, movement, or other type of input distinct from physical aspects of the anatomical movement to be performed or modeled. Further, the input detected in step S1 can include an input from input device 104 (FIG. 1) or user measurement device 108 (FIG. 1), and thus may include detecting a neuronal activity of the user (e.g., by way of an EEG device). Step S1 can also include input device 104 detecting the occurrence of a user-transmitted brain signal (e.g., a measured electrical signal), and then providing an input to computing device 102 based on the occurrence of the user-transmitted brain signal. In an example aspect, detecting a user-transmitted brain signal in step S1 with input device 104 may not include translating the user-transmitted brain signal into a corresponding input, but rather using the detecting event itself as an input from input device 104 to computing device 102. In step S2, system 100 (FIG. 1) can, e.g., through computing device 102, model the simulated anatomical movement. In addition or alternatively, computing device 102 can model the simulated anatomical movement with body part device 128 in step S2 simultaneously with the modeling of the human anatomical movement with a virtual body part.

In step S3, system 100 (FIG. 1) (e.g., through processing engine 116 (FIG. 1) of computing device 102 (FIG. 1)) can compare the simulated human anatomical movement from the user with a model human anatomical movement. In the event that the simulated anatomical movement does not match the model human anatomical movement, system 100 (e.g., through processing engine 116 of computing device 102) can determine the extent to which the simulated anatomical movement differs from the model anatomical movement in step S4. In step S5, system 100 (e.g., through feedback device 130)) can provide either positive or negative sensory feedback to the user based on the extent of the difference determined in step S4. The degrees to which feedback can vary are discussed elsewhere herein in the discussion regarding FIG. 1 and feedback device 130, and may include increasing or decreasing the amount of haptic or other feedforward or feedback based on an accuracy of the simulated anatomical movement, forcibly actuating an extremity of the user, etc. In the event that the simulated anatomical movement matches the model anatomical movement, system 100 can provide sensory feedback to the user indicating that the user provided a correct input controlled movement to system 100. Following the feedback to the user, methods according to an embodiment of the present disclosure can return to step S1 to detect another user input, thereby allowing the methods disclosed herein to be repeated as desired. Although steps S2-S6 are presented in alternative sequential order in FIG. 4, it is understood that the execution of some steps may occur in rapid succession or even simultaneously. Specifically, the calculation of the performance metric S7 (see below) can occur at the same time as feedback is provided to the user in steps S5 or S6.

As system 100 (FIG. 1) provides sensory feedback to the user in step S5 or step S6, system 100 can simultaneously monitor the brain activity of the user with a neural monitoring device, e.g., through user measurement device 108 (FIG. 1). To monitor a user as feedback is provided in steps S5 or S6, user measurement device 108 can include an EEG device or similar instrument, e.g., a PET scanner, an fMRI scanner and/or an MVPA scanner.

System 100 (FIG. 1), e.g., through processing engine 116 (FIG. 1) of computing device 102 (FIG. 1), can also calculate a performance metric based on the comparison between the simulated anatomical movement and the model anatomical movement in step S7. In an example embodiment, computing device 102 can compute the user's percentage accuracy of imitating or opposing the model anatomical movement with one or more previous inputs, and display this metric on display device 106 (FIG. 1).

Embodiments of system 100 (FIG. 1) which include restraint therapy device 152 (FIG. 1) can also include step S8 of providing restraint therapy to one or more extremities of the user. In particular, restraint therapy device 152 of system 100 can restrain a user's extremity where a user desires to exercise or not exercise particular body parts when providing the user input detected in step S1. Methods according to the present disclosure can include alternatively restraint therapy and un-restraint therapy of a user extremity (e.g., by executing or bypassing step S8 in sequence cycles through the method) to customize the user's pre-action therapy.

Figure 5:
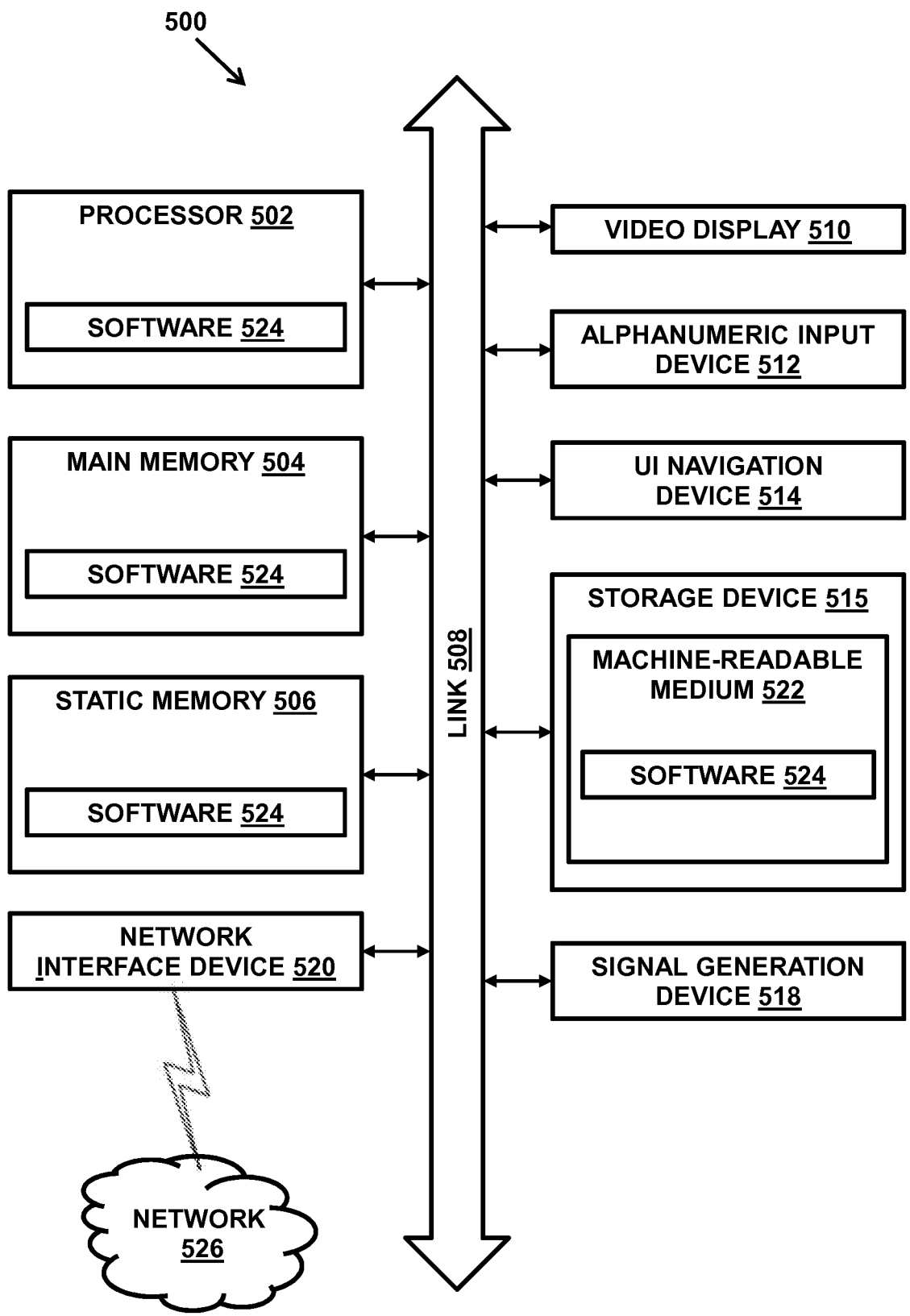
FIG. 5 depicts a block diagram illustrating a machine in the example form of a computer system according to an embodiment of the present disclosure.

FIG. 5 is a block diagram example illustrating a machine in the form of a computer system 500, within which a set or sequence of instructions for causing the machine to perform any one of the methodologies discussed herein may be executed, according to an example embodiment. In alternative embodiments, the machine operates as a standalone device or may be connected (e.g., networked) to other machines. In a networked deployment, the machine may operate in the capacity of either a server or a client machine in server-client network environments, or it may act as a peer machine in peer-to-peer (or distributed) network environments. The machine may be a personal computer ("PC"), a tablet PC, a set-top box ("STB"), a Personal Digital Assistant ("PDA"), a mobile telephone, a web appliance, a network router, switch or bridge, a cloud-based computing device, or any machine capable of executing instructions (sequential or otherwise) that specify actions to be taken by that machine. In an embodiment, computer system 500 can include a digital computing device such as computing device 102 (FIG. 1). Further, while only a single machine is illustrated, the term "machine" shall also be taken to include any collection of machines that individually or jointly execute a set (or multiple sets) of instructions to perform any one or more of the methodologies discussed in the present disclosure.

Example computer system 500 can include at least one processor 502 (e.g., a central processing unit ("CPU"), a graphics processing unit ("GPU"), digital signal processor ("DSP"), custom processor—any or all, processor cores, compute nodes, etc.), a main memory 504 and a static memory 505. Components of computer system 500 communicate with each other via a link 508 (e.g., bus). Computer system 500 may further include a video display unit 510, an alphanumeric input device 512 (e.g., a keyboard), and a user interface ("UI") navigation device 514 (e.g., a mouse). In one embodiment, video display unit 510, input device 512 and UI navigation device 514 are incorporated into a touch screen display. Computer system 500 may additionally include a storage device 515 (e.g., a drive unit), a signal generation device 518 (e.g., a speaker), a network interface device 520, and one or more sensors (not shown), such as a global positioning system ("GPS") sensor, compass, accelerometer, or other sensor.

Computer system 500 may be configured to interface with one or more external devices, such as an input device (e.g., input device 104 (FIG. 1), user measurement device 108 (FIG. 1)), an output device (e.g., display device 106 (FIG. 1), feedback device 130 (FIG. 1), body part device 128 (FIG. 1, or a combination input/output device (e.g., user interface device 160 (FIG. 1)). Specifically, computer system 500 may contain circuitry and/or instructions that allow computer system 500 to connect to and/or communicate with these sub-component or external devices.

Storage device 515 can include a machine-readable medium 522 on which is stored one or more sets of data structures and instructions 524 (e.g., software) embodying or used by any one or more of the methodologies or functions described herein. Instructions 524 may also reside, completely or at least partially, within the main memory 504, static memory 505 and/or within the processor 502 during execution thereof by the computer system 500, with the main memory 504, static memory 506 and the processor 502 constituting machine-readable media.

While the machine-readable medium 522 is illustrated in an example embodiment to be a single medium, the term "machine-readable medium" may include a single medium or multiple media (e.g., a centralized or distributed database, and/or associated caches and servers) that store the one or more instructions 524. The term "machine-readable medium" can include any tangible medium that is capable of storing, encoding or carrying instructions for execution by the machine and that cause the machine to perform any one or more of the methodologies of the present disclosure or that is capable of storing, encoding or carrying data structures used by or associated with such instructions. The term "machine-readable medium" shall accordingly be taken to include, but not be limited to, solid-state memories and optical and magnetic media. Specific examples of machine-readable media include non-volatile memory, including, by way of example, semiconductor memory devices (e.g., Electrically Programmable Read-Only Memory ("EPROM"), Electrically Erasable Programmable Read-Only Memory ("EEPROM")) and flash memory devices; solid state drives ("SSDs"), magnetic disks such as internal hard disks and removable disks; magneto-optical disks; and ROM discs such as CD-ROM, DVD-ROM and Blu-Ray™ discs.

Instructions 524 may further be transmitted or received over a communications network 526 using a transmission medium via the network interface device 520 using any of a number of well-known transfer protocols (e.g., HTTP, XML, FTP). Examples of communication networks include a local area network ("LAN"), a wide area network ("WAN"), the Internet, mobile telephone networks, Plain Old Telephone ("POTS") networks and wireless data networks (e.g., Wi-Fi, 3G and 4G LTE/LTE-A or WiMAX networks) or any combination thereof. The term "transmission medium" can include any intangible medium that is capable of storing, encoding, or carrying instructions for execution by the machine and includes digital or analog communications signals or other intangible medium to facilitate communication of such software.

Examples, as described herein, may include, or may operate on, logic or a number of modules, or mechanisms. Modules are tangible entities capable of performing specified operations and may be configured or arranged in a certain manner. In an example, circuits may be arranged (e.g., internally or with respect to external entities such as other circuits) in a specified manner as a module. In an example, the whole or part of one or more computer systems (e.g., a standalone, client or server computer system) or one or more hardware processors may be configured by firmware or software (e.g., instructions, an application portion, or an application) as a module that operates to perform specified operations. In an example, the software may reside on a non-transitory machine-readable medium or in a transmission signal. In an example, the software, when executed by the underlying hardware of the module, causes the hardware to perform the specified operations.

Accordingly, the terms "module" and "device" are understood to encompass a tangible entity, be that an entity that is physically constructed, specifically configured (e.g., hardwired), or temporarily (e.g., transitory) configured (e.g., programmed) to operate in a specified manner or to perform part or all of any operation described herein. For example, where the modules comprise a general-purpose hardware processor configured using software; the general-purpose hardware processor may be configured as respective different modules at different times and/or different spaces.

Accordingly, software may configure a hardware processor, for example, to constitute a particular module at one instance of time and to constitute a different module at a different instance of time.

As used in this disclosure, the terms "component," "module," "system" and the like are intended to include a computer-related entity, such as but not limited to hardware, firmware, a combination of hardware and software, software, or software in execution. For example, a component may be, but is not limited to being, a process running on a processor, a processor, an object, an executable, a thread of execution, a program and/or a computer. By way of illustration, both an application running on a computing device and the computing device can be a component. One or more components can reside within a process and/or thread of execution and a component may be localized on one computer and/or distributed between two or more computers. In addition, these components can execute from various computer readable media having various data structures stored thereon. The components may communicate by way of local and/or remote processes such as in accordance with a signal having one or more data packets, such as data from one component interacting with another component in a local system, distributed system and/or across a network such as the Internet with other systems by way of the signal.

Moreover, the term "or" is intended to mean an inclusive "or" rather than an exclusive "or." That is, unless specified otherwise, or clear from the context, the phrase "X employs A or B" is intended to mean any of the natural inclusive permutations. That is, the phrase "X employs A or B" is satisfied by any of the following instances: X employs A; X employs B; or X employs both A and B. or clear from the context to be directed to a singular form.

Various aspects or features will be presented in terms of systems that may include a number of devices, components, modules and the like. It is to be understood and appreciated that the various systems may include additional devices, components, modules, etc. and/or may not include all of the devices, components, modules etc. discussed in connection with the figures. A combination of these approaches may also be used.

The various illustrative logics, logical blocks, modules and circuits described in connection with the embodiments disclosed herein may be implemented or performed with a general purpose processor, a digital signal processor ("DSP"), an application specific integrated circuit ("ASIC"), a field programmable gate array ("FPGA") or other programmable logic device, discrete gate or transistor logic, discrete hardware components, or any combination thereof designed to perform the processes described herein. A general-purpose processor may be a microprocessor, but, in the alternative, the processor may be any conventional processor, controller, microcontroller, or state machine. A processor may also be implemented as a combination of computing devices, e.g., a combination of a DSP and a microprocessor, a plurality of microprocessors, one or more microprocessors in conjunction with a DSP core, or any other such configuration. Additionally, at least one processor may comprise one or more modules operable to perform one or more of the steps and/or actions described above.

Further, the steps and/or actions of a method or algorithm described in connection with the aspects disclosed herein may be embodied directly in hardware, in a software module executed by a processor, or in a combination of the two. A software module may reside in RAM memory, flash memory, ROM memory, EPROM memory, EEPROM memory, registers, a hard disk, a removable disk, a CD-ROM, or any other form of storage medium known in the art. An exemplary storage medium may be coupled to the processor, such that the processor can read information from and write information to, the storage medium. In the alternative, the storage medium may be integral to the processor. Further, in some aspects, the processor and the storage medium may reside in an ASIC. Additionally, the ASIC may reside in a user terminal. In the alternative, the processor and the storage medium may reside as discrete components in a user terminal. Additionally, in some aspects, the steps and/or actions of a method or algorithm may reside as one or any combination or set of codes and/or instructions on a machine readable medium and/or computer readable medium, which may be incorporated into a computer program product.

In one or more aspects, the processes described may be implemented in hardware, software, firmware, or any combination thereof. If implemented in software, the processes may be stored or transmitted as one or more instructions or code on a computer-readable medium. Computer-readable media includes both computer storage media and communication media including any medium that facilitates transfer of a computer program from one place to another. A storage medium may be any available media that can be accessed by a computer. By way of example and not limitation, such computer-readable media can comprise RAM, ROM, EEPROM, CD/DVD-ROM or -RW or other optical disk storage, magnetic disk storage or other magnetic storage devices, or any other medium that can be used to carry or store desired program code in the form of instructions or data structures and that can be accessed by a computer. Also, any connection may be termed a computer-readable medium. For example, if software is transmitted from a website, server, or other remote source using a coaxial cable, fiber optic cable, twisted pair, digital subscriber line ("DSL"), or wireless technologies such as infrared, radio and microwave, then the coaxial cable, fiber optic cable, twisted pair, DSL, or wireless technologies such as infrared, radio and microwave are included in the definition of medium. Disk and disc, as used herein, includes magnetic hard-drive ("HD"), solid state drive ("SSD"), compact disc ("CD"), laser disc, optical disc, digital versatile disc ("DVD"), floppy disk and Blu-ray disc where disks usually reproduce data magnetically, while discs usually reproduce data optically with lasers. Combinations of the above should also be included within the scope of computer-readable media.

The terminology used herein is for the purpose of describing particular embodiments only and is not intended to be limiting of the invention. As used herein, the singular forms "a," "an," and "the" are intended to include the plural forms as well, unless the context clearly indicates otherwise. It will be further understood that the terms "comprises" and/or "comprising," when used in this specification, specify the presence of stated features, integers, steps, operations, elements and/or components, but do not preclude the presence or addition of one or more other features, integers, steps, operations, elements, components and/or groups thereof.

The corresponding structures, materials, acts and equivalents of all means or step plus function elements in the claims below are intended to include any structure, material, or act for performing the function in combination with other claimed elements as specifically claimed. The description of the present invention has been presented for purposes of illustration and description but is not intended to be exhaustive or limited to the invention in the form disclosed. Many modifications and variations will be apparent to those of ordinary skill in the art without departing from the scope and spirit of the invention. The embodiment was chosen and described in order to best explain the principles of the invention and the practical application and to enable others of ordinary skill in the art to understand the invention for various embodiments with various modifications as are suited to the particular use contemplated.

We claim:

1. An apparatus for pre-action, body part and related spinal cord, brain stem and neuronal therapies, the apparatus comprising:
   a computing device configured to convert an input control action movement into a simulation instruction, wherein the input control action movement is provided by an input device;
   at least one simulated body part operatively connected to the computing device and configured to simulate at least one modeled human anatomical movement based on the simulation instruction derived from the input control action, wherein the at least one modeled human anatomical movement is a distinct non-corresponding movement from the input control action movement, and wherein the at least one simulated body part comprises a robotic anatomical model configured to simulate the at least one human anatomical movement; and
   a feedback device operatively connected to the computing device and configured to transmit a sensory response, wherein the sensory response is based on the modeled human anatomical movement.

2. The apparatus of claim 1, wherein the feedback device is coupled to a user body part, and wherein the sensory response acts on the user body part to stimulate one or more physical body parts of a user.

3. The apparatus of claim 2, wherein the feedback device comprises means for providing a vibrational feedback to the user.

4. The apparatus of claim 2, wherein the feedback device comprises means for providing an auditory feedback to the user.

5. The apparatus of claim 1, further comprising a restraint therapy device in communication with the feedback device and configured to restrain at least one body part of a user, wherein the feedback device is further configured to control the restraint therapy device to restrain or assist at least one body part of a user.

6. The apparatus of claim 1, wherein the input device includes at least one of a controller, a motion control system, a sensory body harness and an electroencephalography ("EEG") device.

7. The apparatus of claim 6, wherein the input device includes the EEG device, and the EEG device includes at least one of a PET scanner, an fMRI scanner and an MVPA scanner.

8. The apparatus of claim 1, wherein the feedback device comprises a haptic feedback unit operatively connected to the computing device and configured to transmit the sensory response to a user.

9. The apparatus of claim 1, wherein the feedback device comprises an auditory feedback unit operatively connected to the computing device and configured to transmit an auditory stimulation to a user.

10. The apparatus of claim 1 further comprising a video display, and the computing device is configured to display the at least one simulated body part simulating the modeled human anatomical movement on the video display.

11. The apparatus of claim 10, wherein the computing device is configured to display the at least one simulated body part simulating the modeled human anatomical movement as having a full range of human motion.

12. The apparatus of claim 10, wherein the computing device is configured to display the at least one simulated body part simulating the modeled human anatomical movement as a demonstration of a desired modeled human anatomical movement prior to receipt of the input control action movement from a user.

13. The apparatus of claim 1 wherein the computing device is configured to calculate a difference between an ideal movement and the at least one modeled human anatomical movement.

14. The apparatus of claim 13 further comprising a video display screen, and the computing device is configured to display the at least one simulated body part simulating the modeled human anatomical movement on the video display screen, and wherein the computing device is configured to adjust the display of the at least one simulated body part simulating the modeled human anatomical movement on the video display screen based on the calculated difference between an ideal movement and the at least one modeled human anatomical movement.

15. The apparatus of claim 13 wherein the sensory response is varied based on the calculated difference between an ideal movement and the at least one modeled human anatomical movement.

16. The apparatus of claim 13 wherein the computing device is configured to calculate statistics based on the calculated difference between an ideal movement and the at least one modeled human anatomical movement.

17. The apparatus of claim 16 wherein the computing device in configured to adjust a difficulty level of the simulation instruction based on the calculated difference between an ideal movement and the at least one modeled human anatomical movement.

18. A method for pre-action, body part and related spinal cord, brain stem and neuronal therapies, the method comprising: translating an input control action movement into a simulation instruction for at least one modeled human anatomical movement, wherein the at least one modeled human anatomical movement is a distinct non-corresponding movement from the input control action movement; simulating, with at least one simulated body part, the at least one modeled human anatomical movement based on the simulation instruction; calculating a difference between an ideal movement and the at least one modeled human anatomical movement; and transmitting a sensory response to a user, wherein the sensory response is derived from the calculated difference.

19. The method of claim 18, further comprising: translating a cooperative or competing input control action into a simulation instruction for at least one cooperative or competing human anatomical movement; and simulating, with the at least one simulated body part, the at least one cooperative or competing human anatomical movement based on the simulation instruction for the at least one cooperative or competing human anatomical movement.

20. The method of claim 18, further comprising restraining or assisting at least one body part of the user.

21. The method of claim 18, further comprising modifying the sensory response to excite neurons in at least one of a prefrontal cortex, a premotor cortex, a motor cortex, and a supplementary motor area of the user.

22. The method of claim 18, further comprising monitoring a neuronal activity of the user, and converting the monitored neuronal activity into the input control action movement.

23. The method of claim 18, wherein the at least one simulated body part includes at least one of a virtual model and a robotic model.

24. The method of claim 18, further comprising diagnosing a medical condition of the user based on the calculated difference between the ideal movement and the at least one modeled human anatomical movement.

25. A system for pre-action, body part and related spinal cord, brain stem and neuronal therapies, the system comprising:
an input device configured to receive an input control action movement from a user;
at least one simulated body part operatively connected to the input device and configured to simulate at least one modeled human anatomical movement based on the input control action movement;
a feedback device operatively connected to the input device and configured to transmit a sensory response to the user; and
a computing device operatively connected to the input device, the at least one simulated body part and the feedback device, wherein the computing device is configured to perform actions including:
simulate, with the at least one simulated body part, the at least one modeled human anatomical movement based on the input control action movement, wherein the at least one modeled human anatomical movement is a distinct non-corresponding movement from the input control action movement,
calculate a difference between an ideal movement and the modeled human anatomical movement, and
transmit a sensory response via the feedback device to a user, wherein the sensory response is derived from the calculated difference.

26. The system of claim 25, wherein the at least one simulated body part comprises one of a robotic body part and a virtual body part for simulating the modeled human anatomical movement in virtual space, the virtual body part being displayed upon a display device.

27. The system of claim 25, further comprising a restraint therapy device operatively connected to the computing device, wherein the computing device is further configured to instruct the restraint therapy device to restrain or assist at least one body part of the user.

28. The system of claim 25, wherein the feedback device comprises haptic feedback units mechanically coupled to the feedback device and configured to provide the sensory response to the user.

29. The system of claim 25, wherein the input device includes at least one of a controller, a motion control system, a sensory body harness and an electroencephalography device.

30. The system of claim 25, wherein the computing device is further configured to receive at least one cooperative or competing input control action movement from at least one cooperative or competing user, translate the at least one cooperative or competing input control action movement into at least one cooperative or competing simulated human anatomical movement, and simulate the at least one cooperative or competing simulated human anatomical movement with the simulated body part based on the at least one cooperative or competing input control action movement.

31. The system of claim 25 further comprising a second input device configured to receive a second input control action movement from a second user.

32. The system of claim 31, wherein the computing device is further configured to: receive, via the second input device, at least one cooperative input control action movement from the second user; translate the at least one cooperative input control action movement from the second user into at least one cooperative simulated human anatomical movement; and simulate the at least one cooperative simulated human anatomical movement with the simulated body part based on the at least one cooperative input control action movement.

33. The system of claim 31, wherein the computing device is further configured to: receive, via the second input device, at least one competing control action movement from the second user; translate the at least one competing input control action movement into at least one competing simulated human anatomical movement; and simulate the at least one competing simulated human anatomical movement with the simulated body part based on the at least one competing input control action movement.

34. The system of claim 31, wherein the computing device is further configured to: receive, via the second input device, at least one demonstrative input control action movement from the second user; translate the at least one demonstrative input control action movement from the second user into at least one demonstrative simulated human anatomical movement; and simulate the at least one demonstrative simulated human anatomical movement with the simulated body part based on the at least one demonstrative input control action movement from the second user.

35. The system of claim 25 further comprising a second input device configured to receive aa second input control action movement from a second user; the second input device operatively connected to a second computing device; and wherein the second computing device communicates with the computing device via a communications network.

* * * * *